(12) United States Patent
Major et al.

(10) Patent No.: US 12,607,807 B2
(45) Date of Patent: Apr. 21, 2026

(54) ALIGNMENT OF A CONNECTOR INTERFACE

(71) Applicant: INTUITIVE SURGICAL OPERATIONS, INC., Sunnyvale, CA (US)

(72) Inventors: Christopher M. Major, Santa Clara, CA (US); Scot C. Fairchild, Santa Clara, CA (US); Ryan C. Abbott, San Jose, CA (US); David W. Bailey, Portola Valley, CA (US); Edward P. Donlon, San Jose, CA (US); Matthew D. Rohr Daniel, San Francisco, CA (US); Timothy D. Boucher, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 529 days.

(21) Appl. No.: 17/908,191

(22) PCT Filed: Mar. 10, 2021

(86) PCT No.: PCT/US2021/021775
§ 371 (c)(1),
(2) Date: Aug. 30, 2022

(87) PCT Pub. No.: WO2021/183689
PCT Pub. Date: Sep. 16, 2021

(65) Prior Publication Data
US 2023/0143152 A1 May 11, 2023

Related U.S. Application Data

(60) Provisional application No. 62/989,498, filed on Mar. 13, 2020.

(51) Int. Cl.
| | |
|---|---|
| *G02B 6/38* | (2006.01) |
| *A61B 34/00* | (2016.01) |
| *A61B 17/00* | (2006.01) |

(52) U.S. Cl.
CPC ............ *G02B 6/3825* (2013.01); *A61B 34/74* (2016.02); *G02B 6/3873* (2013.01); *G02B 6/3897* (2013.01); *A61B 2017/00477* (2013.01)

(58) Field of Classification Search
CPC ......................... G02B 6/3875; H01R 13/6315
See application file for complete search history.

(56) References Cited

U.S. PATENT DOCUMENTS

| | | | | |
|---|---|---|---|---|
| 4,909,748 A | * | 3/1990 | Kozono | ............ H01R 13/6315 |
| | | | | 439/247 |
| 5,138,679 A | | 8/1992 | Edwards et al. | |

(Continued)

FOREIGN PATENT DOCUMENTS

| | | |
|---|---|---|
| CN | 104508524 A | 4/2015 |
| CN | 105655806 A | 6/2016 |

(Continued)

OTHER PUBLICATIONS

International Preliminary Report on Patentability for Application No. PCT/US2021/021775, mailed Sep. 22, 2022, 9 pages.

(Continued)

*Primary Examiner* — Chad H Smith
(74) *Attorney, Agent, or Firm* — Haynes & Boone, LLP.

(57) ABSTRACT

A floating optical fiber connector interface generally includes a retention bracket, a translating socket slidingly associated with the retention bracket, and a biasing element positioned between the retention bracket and the translating socket. A tab portion may permit translation of the translating socket with respect to the retention bracket, and an aperture configured to receive a carriage optical fiber con- (Continued)

nector. The translating socket may translate with respect to the retention bracket within a plane and may further translate in the insertion direction, and the biasing element may resist translation of the translating socket. An alignment plate may be configured to align an instrument interface for connection to a carriage, including a telescoping standoff operable to position the plate at a first position in which the plate is spaced apart from the carriage and to position the plate at a second position in which the plate is adjacent to the carriage.

20 Claims, 13 Drawing Sheets

(56) References Cited

U.S. PATENT DOCUMENTS

| | | | | |
|---|---|---|---|---|
| 6,159,030 | A | * | 12/2000 | Gawron .............. H01R 13/6315 |
| | | | | 439/247 |
| 6,389,187 | B1 | | 5/2002 | Greenaway et al. |
| 7,772,541 | B2 | | 8/2010 | Froggatt et al. |
| 7,781,724 | B2 | | 8/2010 | Childers et al. |
| 8,900,131 | B2 | | 12/2014 | Chopra et al. |
| 2002/0150342 | A1 | | 10/2002 | Kiani |
| 2011/0053399 | A1 | | 3/2011 | Fahllund et al. |
| 2015/0208922 | A1 | | 7/2015 | Simpson et al. |
| 2017/0010421 | A1 | | 1/2017 | Pitwon et al. |
| 2017/0285276 | A1 | | 10/2017 | Altshuler et al. |
| 2019/0029770 | A1 | | 1/2019 | Bailey |
| 2020/0069389 | A1 | | 3/2020 | Morrissette et al. |

FOREIGN PATENT DOCUMENTS

| | | | |
|---|---|---|---|
| CN | 108885315 | A | 11/2018 |
| EP | 1096617 | A1 | 5/2001 |
| EP | 3514894 | A1 | 7/2019 |
| JP | 3390697 | B2 | 3/2003 |
| WO | WO-2016191298 | A1 | 12/2016 |
| WO | WO-2019018736 | A2 | 1/2019 |
| WO | WO-2019027922 | A1 | 2/2019 |
| WO | WO-2020072917 | A1 | 4/2020 |

OTHER PUBLICATIONS

Extended European Search Report for Application No. EP21768008.1, mailed on Mar. 14, 2024, 09 pages.
International Search Report and Written Opinion for Application No. PCT/US2021/021775, mailed on Aug. 17, 2021, 18 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Office Action for Chinese Application No. CN202180019321, mailed Jun. 12, 2025, 16 pages.

* cited by examiner

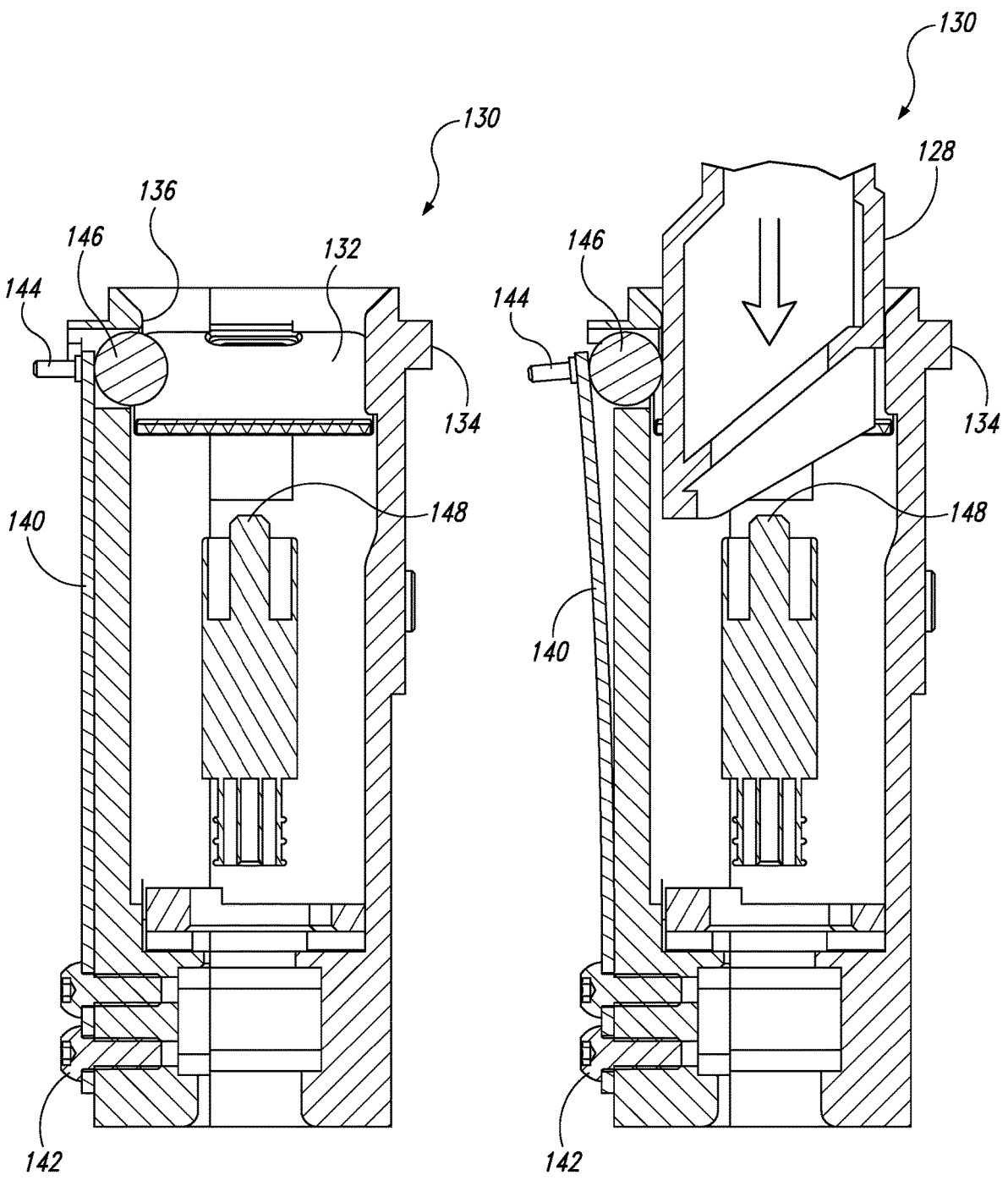
*Fig. 4E*          *Fig. 4F*

ALIGNMENT OF A CONNECTOR INTERFACE

CROSS-REFERENCE TO RELATED APPLICATION(S)

This present application is the U.S. National Phase of International Application No. PCT/US2021/021775, filed Mar. 10, 2021, which designated the U.S. and claims priority to U.S. Provisional Patent Application No. 62/989,498, titled "ALIGNMENT OF A CONNECTOR INTERFACE," filed Mar. 13, 2020, the disclosures of which are incorporated by reference herein in their entirety.

TECHNICAL FIELD

The present technology generally relates to alignment of connectors and, more specifically, to aiding alignment of connectors and/or reducing particle formation at a non-permanent connection joint.

BACKGROUND

Minimally invasive medical techniques are intended to reduce an amount of tissue that is damaged during medical procedures, thereby reducing patient recovery time, discomfort, and harmful side effects. Such minimally invasive techniques may be performed through natural orifices in a patient anatomy or through one or more surgical incisions. An operator (e.g., a physician) may insert minimally invasive medical instruments (surgical, diagnostic, therapeutic, biopsy instruments, etc.) through these natural orifices or incisions to reach a target tissue location. One such minimally invasive technique is to use a flexible and/or steerable elongate device, such as a flexible catheter, that can be inserted into anatomic passageways and navigated toward a region of interest within the patient anatomy. Control of such an elongate device by an operator involves the management of several degrees of freedom including at least the management of insertion and retraction of the elongate device with respect to the patient anatomy, as well as steering of the device.

Communication signals may be transmitted between components of a medical system using various cables, including optical fibers, coaxial conductors, copper conductors, twisted wire pairs, etc. The joining of communication cables can be performed using a variety of connectors. When using optical fibers for communication signals, it is desirable to form a low loss joint, by abutting faces at the cleaved ends of the fibers with precise alignment of the fiber cores. For non-permanent connectors of optical fibers, the cleaved ends of the fibers are held in alignment by a mechanical force. The signals transmitted by the optical fiber cable can be degraded by contamination between the mating faces at the joint. Forming the optical fiber connection with such contamination can cause damage to the faces over time and result in permanent performance reduction as particles are embedded in the fiber face.

SUMMARY

In accordance with an embodiment of the present technology, a floating connector interface is provided. The floating interface generally includes a retention bracket having a slot, a translating socket slidingly associated with the retention bracket, and a biasing element positioned between the retention bracket and the translating socket. The translating socket may include a tab portion extending into the slot to permit translation of the translating socket with respect to the retention bracket, and an aperture configured to receive a carriage connector. The translation of the translating socket may be confined within a floating plane, and the biasing element may be configured to resist the translation of the translating socket.

In accordance with another embodiment of the present technology, a carriage is provided. The carriage generally includes a retention bracket having a slot, a translating socket slidingly associated with the retention bracket, a carriage connector having a housing that may be removably couplable to an aperture in the translating socket, and a biasing element positioned between the retention bracket and the translating socket. The translating socket may include a tab portion extending into the slot to permit translation of the translating socket with respect to the carriage, where the translation may be confined within a floating plane. The biasing element may be configured to resist the translation of the translating socket, and a direction of insertion of an instrument connector into the carriage connector may be normal to the floating plane.

In accordance with another embodiment of the present technology, a connector alignment apparatus is provided. The connector alignment apparatus generally includes a carriage having a carriage optical fiber connector, a plate configured to removably retain an instrument interface in alignment for connection to the carriage, and a telescoping standoff coupled between the plate and the carriage. The plate may have an aperture configured to receive an instrument optical fiber connector, and the telescoping standoff may be operable to position the plate at a first position in which plate is spaced apart from the carriage and to position the plate at a second position in which the plate is adjacent to the carriage.

In accordance with another embodiment of the present technology, an alignment system is provided. The alignment system generally includes a carriage having a housing and a carriage optical fiber connector, an instrument interface having an outer surface and an instrument optical fiber connector configured to connect to the carriage optical fiber connector when the instrument interface is mated to the carriage, and an alignment spar protruding from the housing of the carriage. The alignment spar may have a shape corresponding to the outer surface of the instrument interface and may be configured to align the instrument interface and the carriage such that the instrument optical fiber connector is aligned with the carriage optical fiber connector.

In accordance with another embodiment of the present technology, an instrument is provided. The instrument generally includes an instrument interface and an instrument optical fiber connector protruding from the instrument interface. The instrument optical fiber connector may include a connector body having an outer surface configured to interface with a carriage optical fiber connector, and a conical kinematic surface positioned on a distal end portion of the connector body. The conical kinematic surface may taper down from the outer surface of the connector body to a tip of the connector body. The conical kinematic surface may be configured to align the instrument optical fiber connector and the carriage optical fiber connector during installation of the instrument interface.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

FIGS. 4E and 4F are cross sectional side views of the carrier optical fiber connector of FIG. 4A, showing a friction-reducing roller positioned on at least one side of a connector well.

Figure 1A:
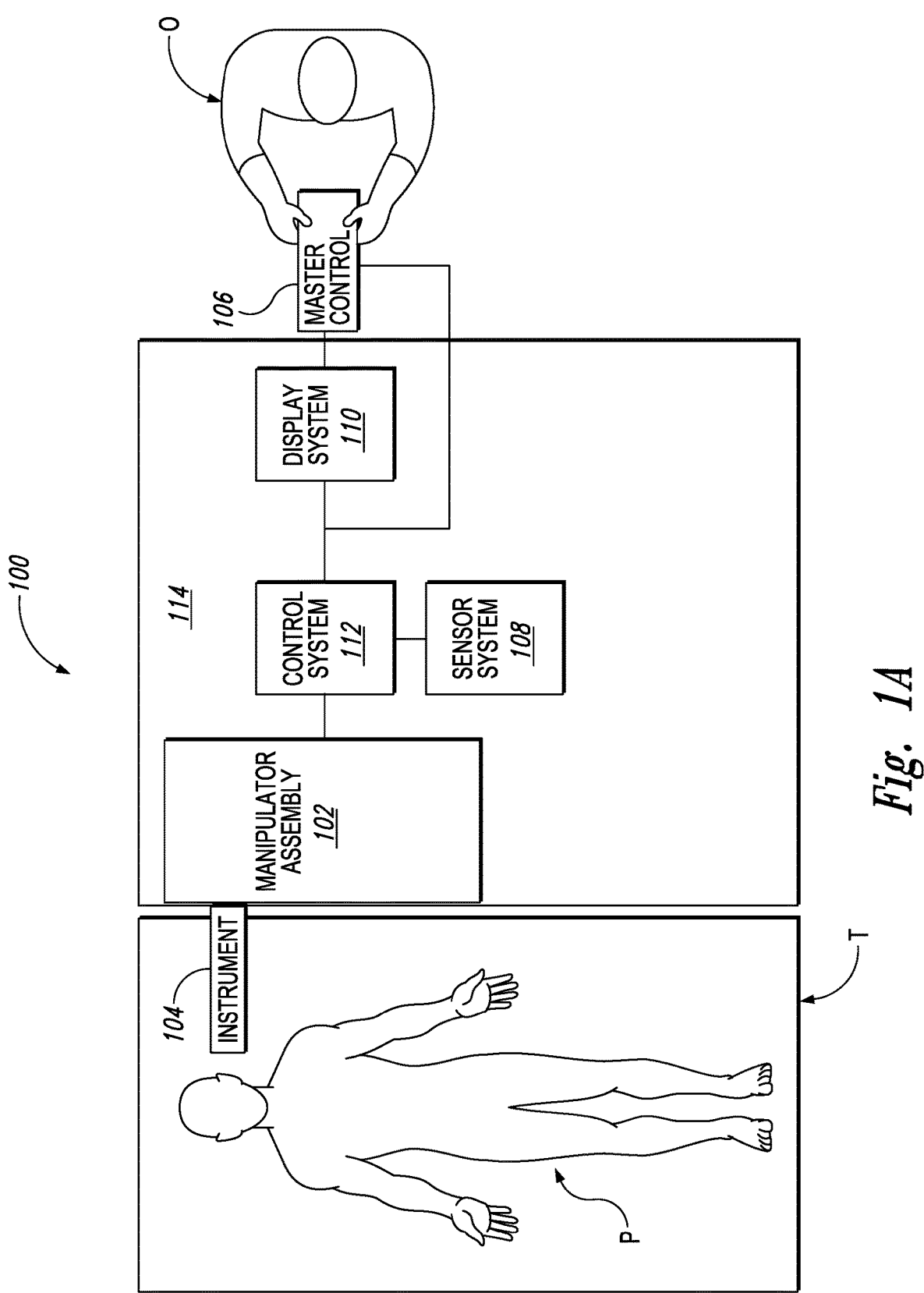
FIG. 1A is a simplified diagram of a medical system configured in accordance with an embodiment of the present technology.

Embodiments of the present technology and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The present technology generally relates to alignment of a connector interface, e.g., between ends of optical fibers to reduce particle formation at a non-permanent optical fiber connection joint. Various medical systems may include optical fiber connectors configured to receive an optical fiber connector positioned on one or more modular medical instruments. To aid insertion of the optical fiber connectors, the system connectors may be designed such that there is forgiveness in multiple degrees of freedom and an operator is not required to perfectly align the instrument during installation. Preventing misalignment of the connectors during installation may reduce the potential of damage to the optical fiber, generate fewer contaminants, and allow the ends of the fibers to make a proper and complete connection.

The present disclosure describes various instruments and portions of instruments in terms of their state in three-dimensional space. As used herein, the term position refers to the location of an object or a portion of an object in a three-dimensional space (e.g., three degrees of translational freedom along Cartesian X-, Y-, and Z-coordinates). As used herein, the term orientation refers to the rotational placement of an object or a portion of an object (e.g., three degrees of rotational freedom, such as roll, pitch, and yaw). As used herein, the term pose refers to the position of an object or a portion of an object in at least one degree of translational freedom and to the orientation of that object or portion of the object in at least one degree of rotational freedom (e.g., up to six total degrees of freedom). As used herein, the term shape refers to a set of poses, positions, or orientations measured along an object.

Figure 1B:
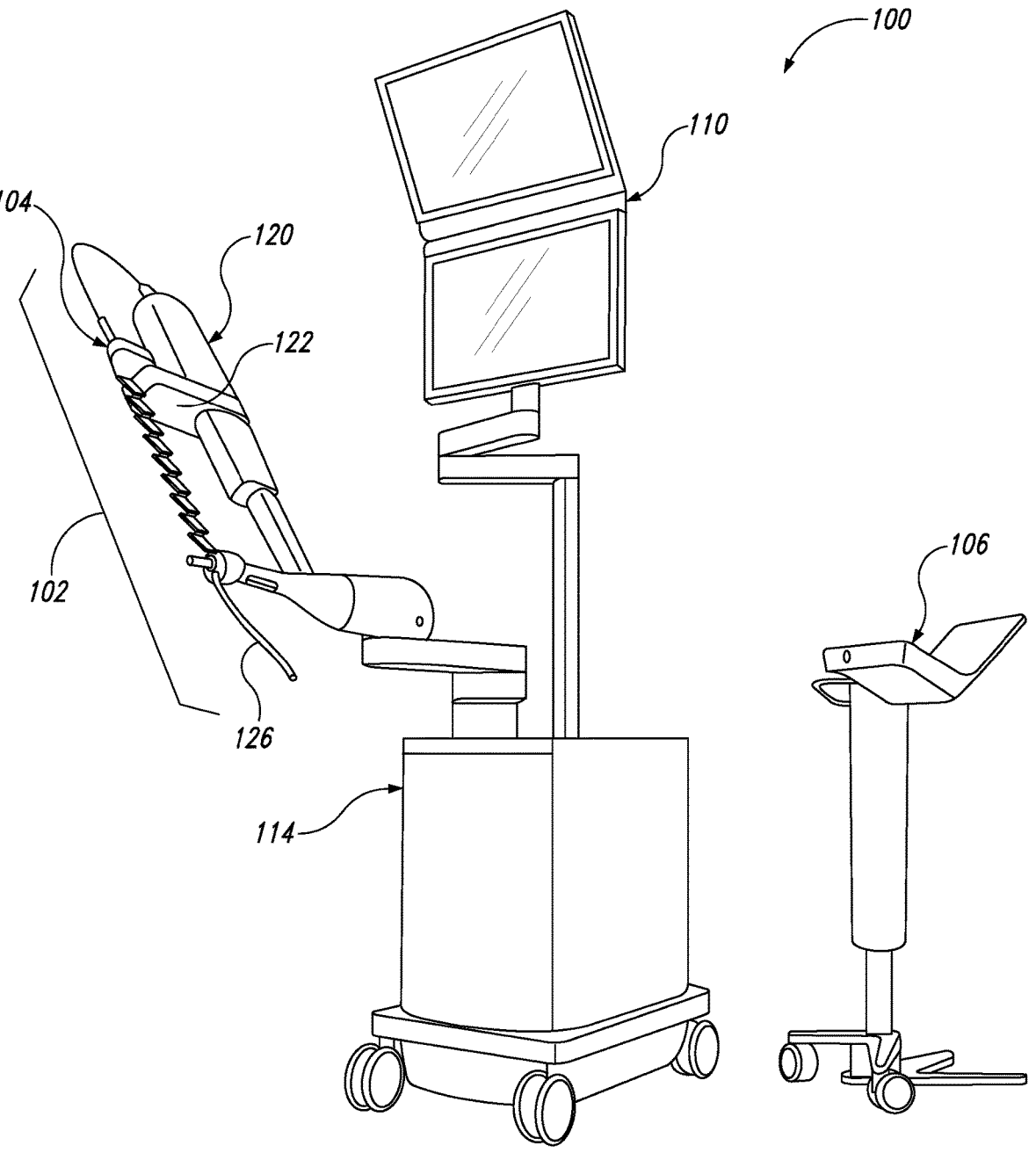
FIG. 1B is a perspective view of a structural representation of the medical system of FIG. 1A.

FIG. 1A is a simplified diagram of a medical system ("system 100") and FIG. 1B is a perspective view of the system 100 configured in accordance with embodiments of the present technology. The system 100 may be suitable for use in surgical, diagnostic, therapeutic, or biopsy procedures, among others. While some embodiments of the system 100 are described herein with respect to such procedures, references to specific medical or surgical instruments and medical or surgical methods is not intended to limit the scope of the present technology. The systems, instruments, and methods described herein may be used for humans, animals, human cadavers, animal cadavers, portions of human or animal anatomy, and/or non-surgical diagnosis, as well as industrial systems and general robotic or teleoperational systems.

As shown in FIGS. 1A and 1B, the system 100 generally includes a manipulator assembly 102 having an instrument manipulator 120 (see FIG. 1B) to manipulate a medical instrument 104 while performing various procedures on a patient P. The manipulator assembly 102 may be teleoperated, non-teleoperated, or a hybrid teleoperated and non-teleoperated assembly with select degrees of freedom of motion that may be motorized and/or teleoperated, and select degrees of freedom of motion that may be non-motorized and/or non-teleoperated. The manipulator assembly 102 can be mounted to an operating table T, or to a main support 114 (e.g. a movable cart, stand, second table, etc.). The system may include a master control 106 configured to allow an operator O (e.g., a surgeon, clinician, physician, etc.) to view the interventional site and to control the manipulator assembly 102.

The master control 106 of the system 100 may be located near or in the same room as the operating table T. In some embodiments, for example, the master control 106 is positioned near the side of a surgical table T on which the patient P is located. However, it should be understood that the operator O can be located in a different room or any distance away from the patient P. The master control 106 generally includes one or more input and control devices (not shown)

for controlling the medical instrument 104 via the instrument manipulator 120. The input and control devices may include any number of a variety of input devices, such as joysticks, trackballs, data gloves, trigger-guns, hand-operated controllers, voice recognition devices, body motion or presence sensors, etc. The input and control devices may be provided with the same degrees of freedom as the associated medical instrument to take advantage of the familiarity of the operator O in directly controlling like instruments. In this regard, the control devices may provide the operator O with telepresence or the perception that the control devices are integral with the medical instruments. However, the input and control devices may have more or fewer degrees of freedom than the associated medical instrument 104 and still provide operator O with telepresence. In some embodiments, the control devices may optionally be manual input devices that move with six degrees of freedom, and which may also include an actuatable handle for actuating instruments (e.g., for closing grasping jaws, applying an electrical potential to an electrode, delivering a medicinal treatment, etc.).

The input and control devices of the master control 106 may include a scroll wheel and a trackball. In an example implementation of the system 100, the scroll wheel may be rolled forwards or backwards in order to control the advancement or retraction of the medical instrument 104 with respect to the patient anatomy, and the trackball may be rolled in various directions by the operator O to steer the position of the distal end portion and/or distal tip of the medical instrument 104, e.g., to control bend or articulation. Various systems and methods related to motion control consoles are described in PCT Pub. No. 2019/027922 (filed Jul. 30, 2018, titled "Systems and Methods for Safe Operation of a Device"), and U.S. Patent Pub. No. 2019/0029770 (filed Jul. 30, 2018, titled "Systems and Methods for Steerable Elongate Device"), which are incorporated by reference herein in their entireties.

As shown in FIG. 1B, the instrument manipulator 120 may be configured to support and manipulate the medical instrument 104 with a kinematic structure of one or more non-servo-controlled links (e.g., one or more links that may be manually positioned and locked in place, generally referred to as a set-up structure (SUS)), and/or one or more servo-controlled links (e.g., one or more powered links that may be controlled in response to commands). The instrument manipulator 120 may include a plurality of actuators or motors that drive inputs on the medical instrument 104 in response to commands from a control system 112. The actuators may include drive systems that when coupled to the medical instrument 104 may advance the medical instrument 104 into a naturally or surgically created anatomic orifice in the patient P. In some embodiments, the kinematic structure may be locked in place or unlocked to be manually manipulated by the operator O interacting with switches, buttons, or other types of input devices.

The instrument manipulator 120 may be configured to position the medical instrument 104 at an optimal position and orientation relative to patient anatomy or other medical devices. In this regard, drive systems may be included in the instrument manipulator 120 to move the distal end of the medical instrument 104 according to any intended degree of freedom, which may include three degrees of linear motion (e.g., linear motion along the X, Y. and/or Z Cartesian axes) and three degrees of rotational motion (e.g., rotation about the X, Y, and Z Cartesian axes). Additionally, the actuators can be used to actuate an articulable end effector (not shown) of the medical instrument 104 for grasping tissue in the jaws of a biopsy device or the like. Actuator position sensors, such as resolvers, encoders, potentiometers, and other mechanisms, may provide sensor data to the system 100 describing the rotation and orientation of the motor shafts of the instrument manipulator 120. Such position sensor data may be used to determine motion of the objects manipulated by the actuators.

In some embodiments, the optimal location and orientation can include alignment of the manipulator assembly 102 with respect to anatomy of the patient P, for example, to minimize friction of the medical instrument 104 positioned within the anatomy of the patient P (e.g. in anatomical openings, patient vasculature, patient endoluminal passageways, etc.), or within medical devices coupled to patient anatomy (e.g. cannulas, trocars, endotracheal tubes (ETT), laryngeal esophageal masks (LMA), etc.). Optimal location and orientation of the manipulator assembly 102 can additionally or alternatively include optimizing the ergonomics for the operator O by providing sufficient workspace and/or ergonomic access to the medical instrument 104 when utilizing various medical tools such as needles, graspers, scalpels, grippers, ablation probes, visualization probes, etc. with the medical instrument 104.

Each adjustment of the manipulator assembly 102 (e.g., insertion, rotation, translation, etc.) can be actuated by either robotic control or by manual intervention by the operator O. For example, each rotational or linear adjustment may be maintained in a stationary configuration using brakes. In this regard, depression of one or more buttons and switches releases one or more corresponding brakes, allowing the operator O to manually position the medical instrument 104 through positioning of the instrument manipulator 120. One or more adjustments may also be controlled by one or more actuators (e.g., motors) such that an operator may use a button or switch to actuate a motor to alter the manipulator assembly 102 in a desired manner to position the manipulator assembly 102 in the optimal position and orientation. In some embodiments, robotic control of the manipulator assembly 102 can be actuated by activating a button or switch. In one example, one position of the button or switch may initiate powered rotation of the manipulator assembly 102 in a first direction of rotation and another position of the button or switch may initiate powered rotation of the manipulator assembly 102 in the other direction.

The manipulator assembly 102 may be configured such that when a button or switch is activated, the operator O may adjust the instrument manipulator 120 along a linear path that corresponds to inserting or retracting the medical instrument 104. For safety purposes, the manipulator assembly 102 might only be manually movable in one translation direction, such as retraction, and might not be manually movable in the direction of insertion of the medical instrument 104, to prevent the operator O from inadvertently or undesirably advancing the medical instrument into the anatomy of the patient O.

As shown in FIG. 1A, the system 100 may include a sensor system 108 with one or more sub-systems for receiving information about the instruments coupled to the instrument manipulator 120. Such sub-systems may include a position/location sensor system (e.g., an electromagnetic (EM) sensor system); a shape sensor system for determining the position, orientation, speed, velocity, pose, and/or shape of a distal end, and/or of one or more segments along a flexible body that may make up a portion of the medical instrument 104; and/or a visualization system for capturing images from the distal portion of the medical instrument 104, among other possible sensors.

Referring again to FIGS. 1A and 1B together, the system 100 also may include a display system 110 for displaying an image or representation of the surgical site and the medical instrument 104 generated the sensor system 108, recorded pre-operatively or intra-operatively. The display system 110 may use image data from imaging technology and/or a real time image, such as by computed tomography (CT), magnetic resonance imaging (MRI), fluoroscopy, thermography, ultrasound, optical coherence tomography (OCT), thermal imaging, impedance imaging, laser imaging, nanotube X-ray imaging, endoscopic images, and the like, or combinations thereof. The pre-operative or intra-operative image data may be presented as two-dimensional, three-dimensional, or four-dimensional (including e.g., time based or velocity-based information) images and/or as images from models created from the pre-operative or intra-operative image data sets. The display system 110 and the master control 106 may be oriented such that the operator O can control the medical instrument 104 and the master control 106 with the perception of telepresence.

The display of visual indicators, markers, and or images on the display system 110 may be altered by input devices (e.g., buttons, switches, etc.) on the manipulator assembly 102 and/or the master control 106. For example, actuating button or switch can cause a marker to be placed in a rendered model of patient anatomy displayed on the display system 110. The marker could correspond to an area within the patient at which a procedure (e.g., biopsy) has been performed, or otherwise indicate an actual location within the patient anatomy where the medical instrument has been positioned. Such a virtual navigational marker may be dynamically referenced with registered preoperative or concurrent images or models. Systems and methods for registration are provided in PCT Pub. No. WO 2016/191298 (published Dec. 1, 2016, titled "Systems and Methods of Registration for Image Guided Surgery"), and in U.S. Pat. No. 8,900,131 (filed May 13, 2011, titled "Medical System Providing Dynamic Registration of a Model of an Anatomic Structure for Image-Guided Surgery"), which are incorporated by reference herein in their entireties.

The control system 112 may include at least one memory and at least one computer processor (not shown) for effecting control between the medical instrument 104, the master control 106, the sensor system 108, and the display system 110. The control system 112 may also include programmed instructions, which may be stored on a non-transitory machine-readable medium, to implement some or all of the methods described in accordance with aspects of the present technology disclosed herein, including instructions for providing information to the display system 110. The control system 112 may include two or more data processing circuits with one portion of the processing optionally being performed on or adjacent to the manipulator assembly 102, another portion of the processing being performed at the master control 106, etc. The processors of the control system 112 may execute instructions for the processes disclosed herein. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, the control system 112 supports wireless communication protocols, such as Bluetooth, IrDA, HomeRF, IEEE 802.11, DECT, Wireless Telemetry, and the like. The control system 112 may receive force and/or torque feedback from the medical instrument 104. In response, the control system 112 may transmit signals to the master control 106. In some embodiments, the control system 112 may transmit signals instructing one or more actuators of the manipulator assembly 102 to move the medical instrument 104. The medical instrument 104 may extend into an internal surgical site within the body of patient P via openings in the body of patient P. Any suitable conventional and/or specialized actuators may be used with the manipulator assembly 102. The one or more actuators may be separate from, or integrated with, the manipulator assembly 102. In some embodiments, the one or more actuators and the manipulator assembly 102 are provided as part of the main support 114, which can be positioned adjacent to the patient P and the operating table T. In some embodiments, the manipulator assembly 102, control system 112, sensor system 108, and display system 110 may be supported by the main support 114, or some or all of these components may be integrated into the main support 114. Alternatively, one or more of these components may be mounted to the operating table T or integrated into the master control 106.

The control system 112 may further include a virtual visualization system to provide navigation assistance to the operator O when controlling the medical instrument 104 during an image-guided surgical procedure. Virtual navigation using the virtual visualization system may be based upon reference to an acquired preoperative or intraoperative dataset of anatomic passageways. During a virtual navigation procedure, the sensor system 108 may be used to compute an approximate location of the medical instrument 104 with respect to the anatomy of the patient P. The location can be used to produce both macro-level tracking images (external to the anatomy of patient P) and virtual images (internal to the anatomy of patient P). The control system 112 may implement one or more EM sensor, fiber optic sensors, and/or other sensors to register and display a medical implement together with preoperatively recorded surgical images, such as those from a virtual visualization system. For example, PCT Pub. No. WO 2016/191298 (published Dec. 1, 2016, titled "Systems and Methods of Registration for Image Guided Surgery"), which is incorporated by reference herein in its entirety, discloses one such system. Various systems and methods for monitoring the shape and relative position of an optical fiber in three dimensions are described in U.S. Pat. No. 7,781,724 (tiled Sep. 26, 2006, titled "Fiber Optic Position and Shape Sensing Device and Method Relating Thereto"); U.S. Pat. No. 7,772,541 (filed on Mar. 12, 2008, titled "Fiber Optic Position and/or Shape Sensing Based on Rayleigh Scatter"); and U.S. Pat. No. 6,389,187 (filed on Jun. 17, 1998, titled "Optical Fiber Bend Sensor"), which are all incorporated by reference herein in their entireties.

The system 100 may further include optional operations and support systems (not shown) such as illumination systems, steering control systems, irrigation systems, and/or suction systems. In some embodiments, the system 100 may include more than one manipulator assembly and/or more than one master control. The exact number of teleoperational manipulator assemblies can be tailored for the surgical procedure to be performed and/or the space constraints within the operating room, among other factors. Multiple master controls may be collocated or positioned in separate locations. Multiple master controls allow more than one operator to control one or more teleoperational manipulator assemblies in various combinations.

The instrument manipulator 120 can be configured to support and position an elongate device 126 of the medical instrument 104. Various elongate devices are described in PCT Pub. No. WO 2019/018736 (filed Jul. 20, 2018, titled "Flexible Elongate Device Systems and Methods"), which is incorporated by reference herein in its entirety.

Figure 2A:
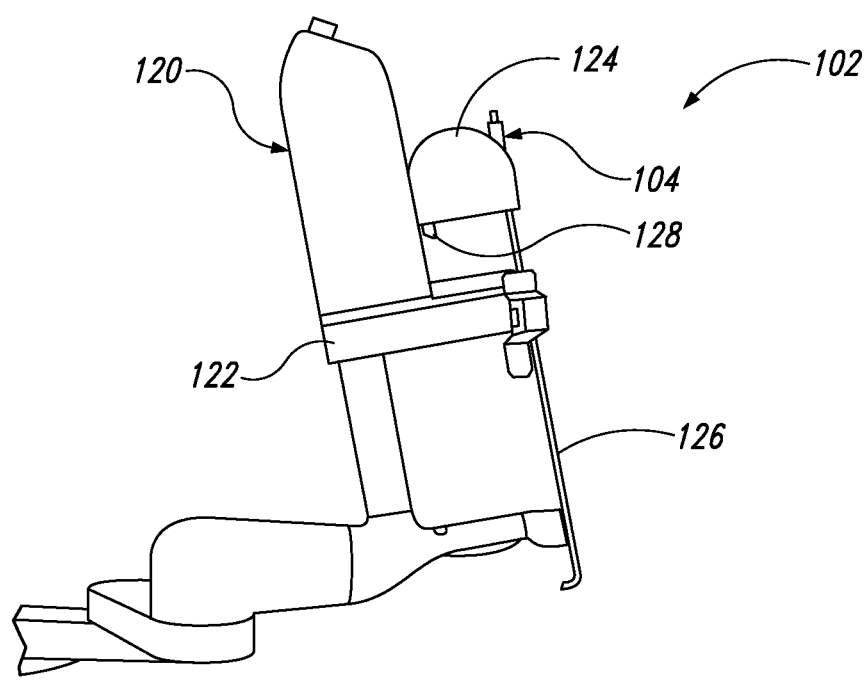
FIGS. 2A and 2B are left side views of a manipulator assembly and medical instrument of the medical system of FIG. 1B.
Figure 2B:
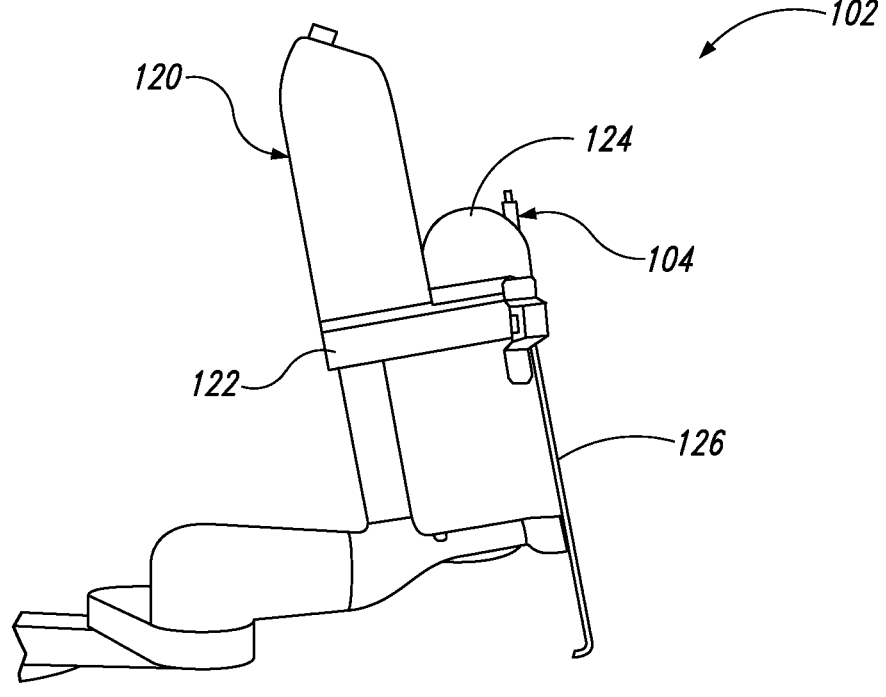

FIGS. 2A and 2B are left side views of the manipulator assembly 102 of the system 100 configured in accordance with embodiments of the present technology. The manipulator assembly 102 generally includes the instrument manipulator 120, which has a carriage 122 for mounting one or more instruments. The carriage 122, for example, may be configured to receive an instrument interface 124 of the medical instrument 104 such that the medical instrument 104 is selectively coupled to the instrument manipulator 120 before conducting a medical operation. FIG. 2A shows the medical instrument 104 having an instrument optical fiber connector 128 protruding from the instrument interface 124, uninstalled from the carriage 122; and FIG. 2B shows the medical instrument 104 installed with the carriage 122. When the medical instrument 104 is installed with the carriage 122, at least a portion of the elongate device 126 extends beyond the carriage 122 to interface with the patient P (not shown) and may be manipulated by the instrument manipulator 120 during use of the system 100 (FIGS. 1A and 1B). In this regard, the instrument manipulator 120 may be configured for insertion and retraction of the elongate device 126 with respect to the patient anatomy by moving in a telescoping manner relative to the patient, and may affect other movements within the degrees of freedom of the elongate device 126. Various manipulation configurations related to a manipulator assembly are described in PCT Application No. PCT/US19/54718 (filed Oct. 4, 2019, titled "Systems and Methods for Positioning Medical Instruments"), which is incorporated by reference herein in its entirety.

Figure 3:
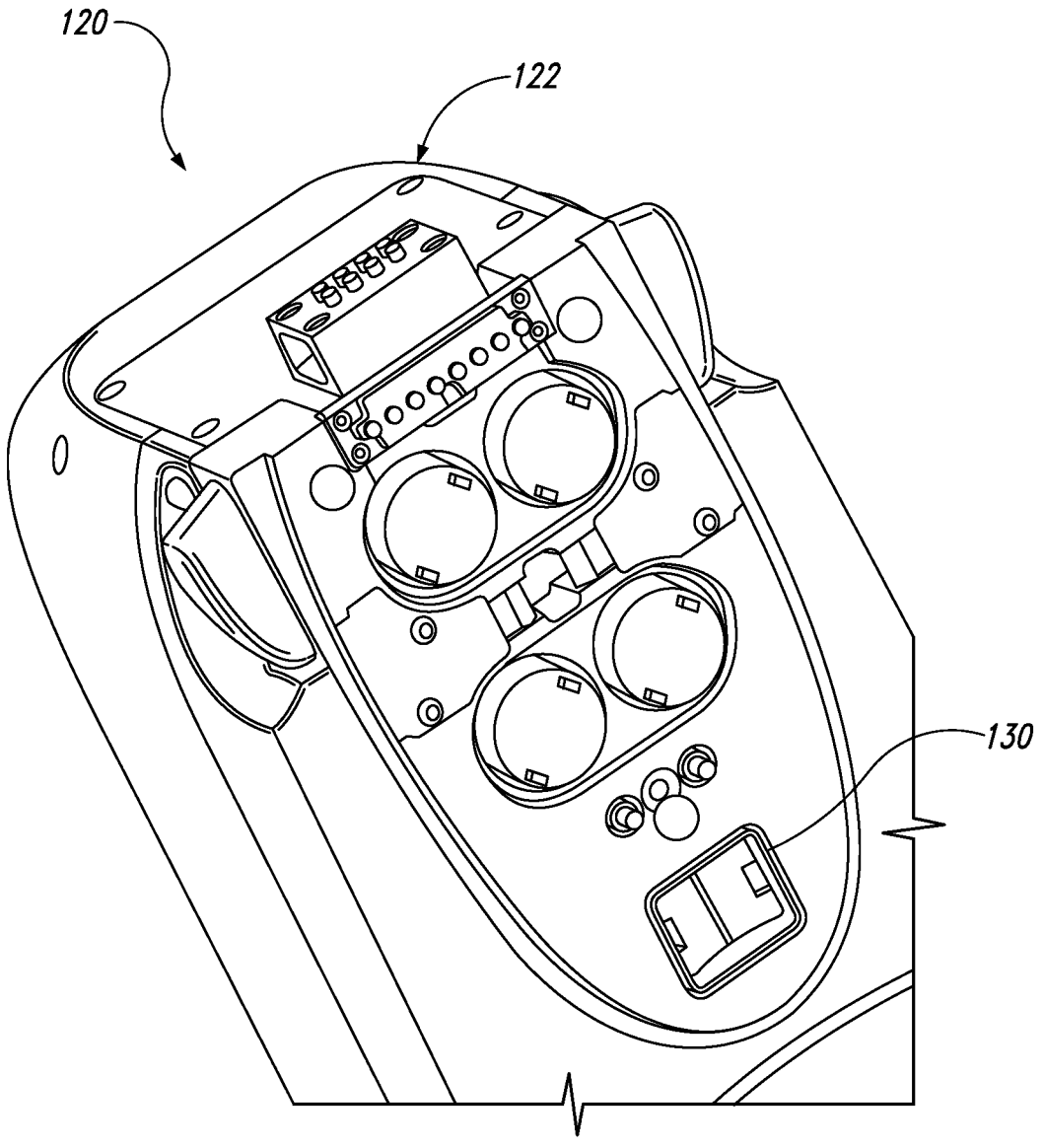
FIG. 3 is a perspective view of a carriage of the teleoperated medical system of FIG. 1B showing a carriage optical fiber connector.

FIG. 3 is a perspective view of a portion of the carriage 122 of the instrument manipulator 120 prior to installation of the instrument interface 124 (e.g., as shown in FIG. 2A). As noted above, the carriage 122 of the instrument manipulator 120 may be configured to receive the instrument interface 124 (FIGS. 2A and 2B) and may include a plurality of actuators or motors that drive corresponding inputs on the instrument interface 124 in response to commands from the control system 112 (FIG. 1A). As shown, the carriage 122 further includes a shuttered carriage optical fiber connector ("carriage optical fiber connector 130") configured to receive the instrument optical fiber connector 128. The carriage optical fiber connector 130 may be configured to be engaged with a floating fiber interface to enable easy connection of an optical fiber with forgiveness in multiple degrees of freedom, as will be explained in greater detail below with reference to FIGS. 4A-5. Thus, referring to FIGS. 2A, 2B, and 3 together, when the instrument optical fiber connector 128 is inserted into and connected to the carriage optical fiber connector 130 of the instrument interface 124, the operator O might not be required to perfectly align the end of the instrument optical fiber connector 128 during insertion, thereby providing flexibility to the operator O. The floating interface may also prevent misalignment of the connectors, thereby reducing the potential of damage to the optical fiber(s), and allowing the cleaved ends of the optical fiber(s) to make a proper and complete connection.

Figure 4A:
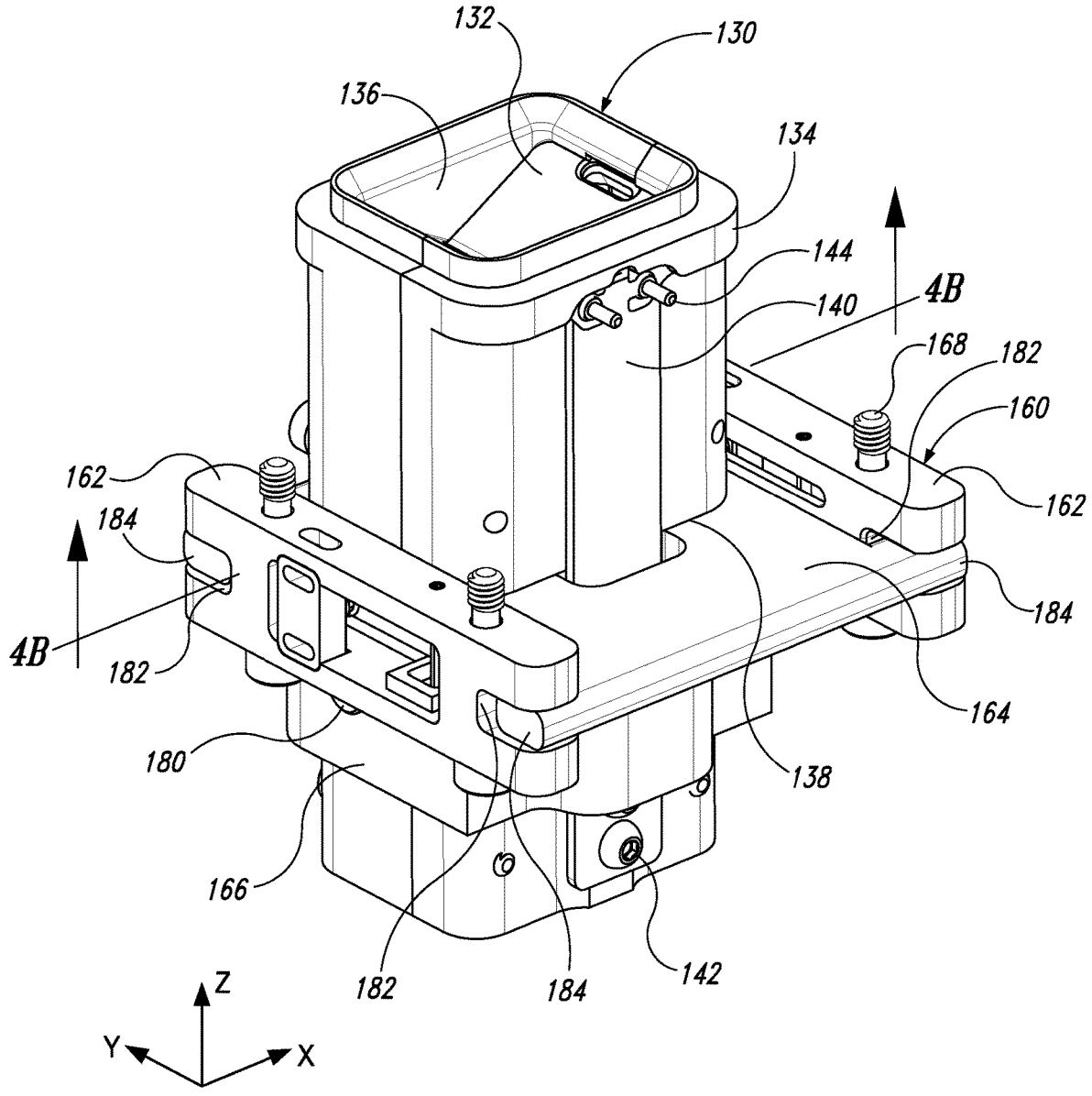
FIG. 4A is a perspective view of a carrier optical fiber connector and a floating fiber interface of the medical system of FIG. 1B configured in accordance with embodiments of the present technology.
Figure 4B:
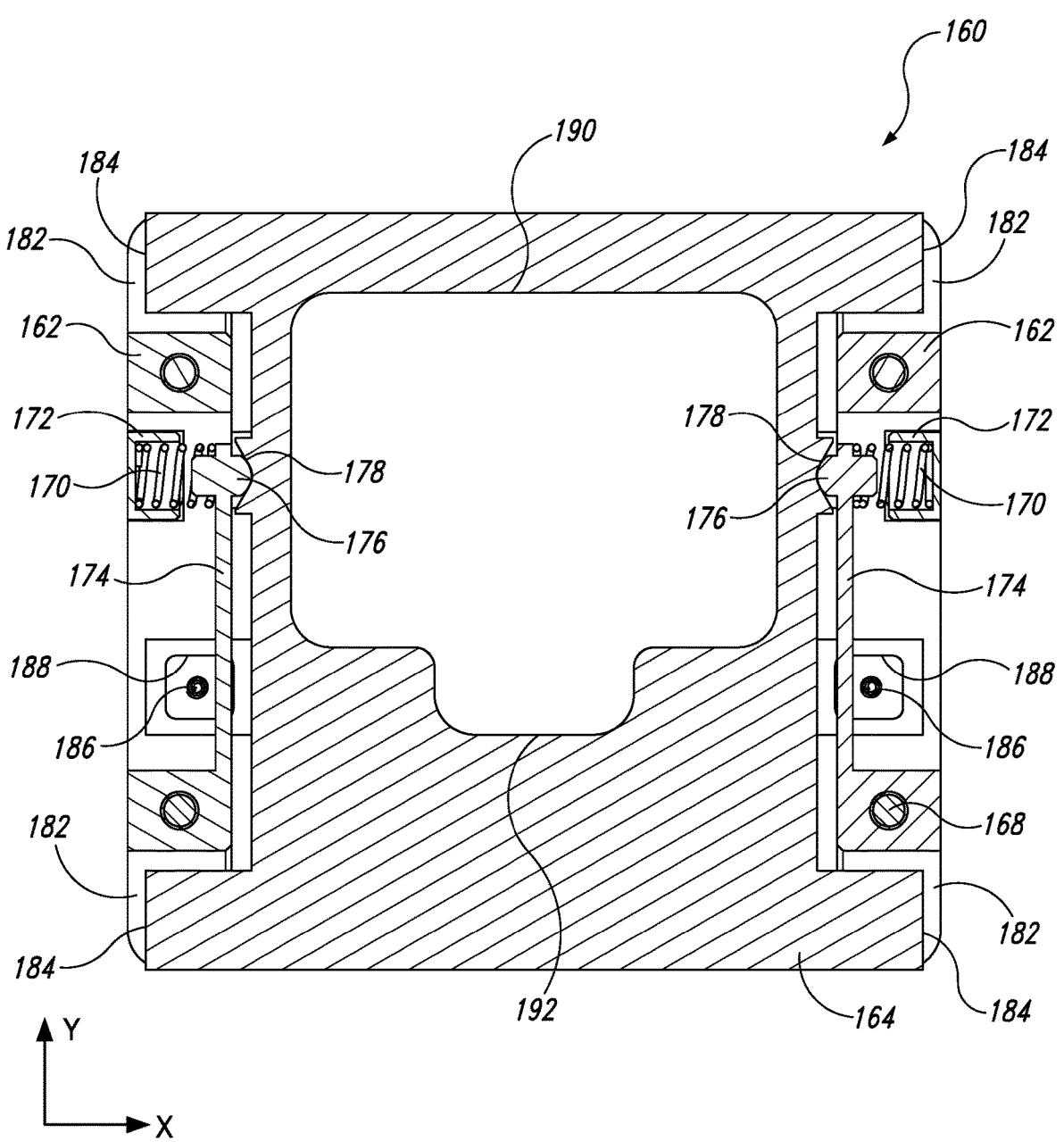
FIG. 4B is a cross sectional plan view of the floating fiber interface of FIG. 4A.
Figures 4C, 4D:
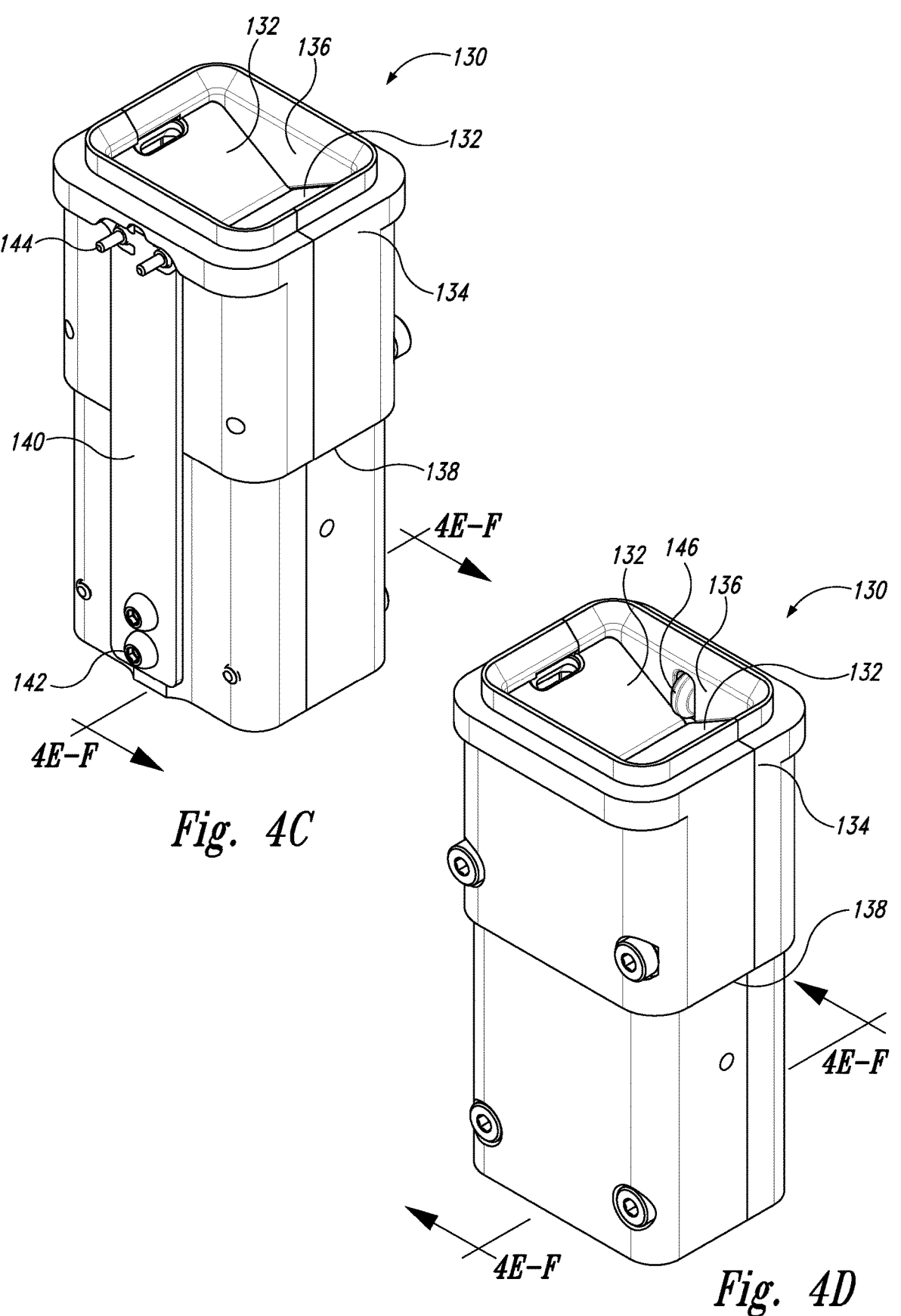
FIGS. 4C and 4D are perspective views of the carrier optical fiber connector of FIG. 4A.
Figure 5:
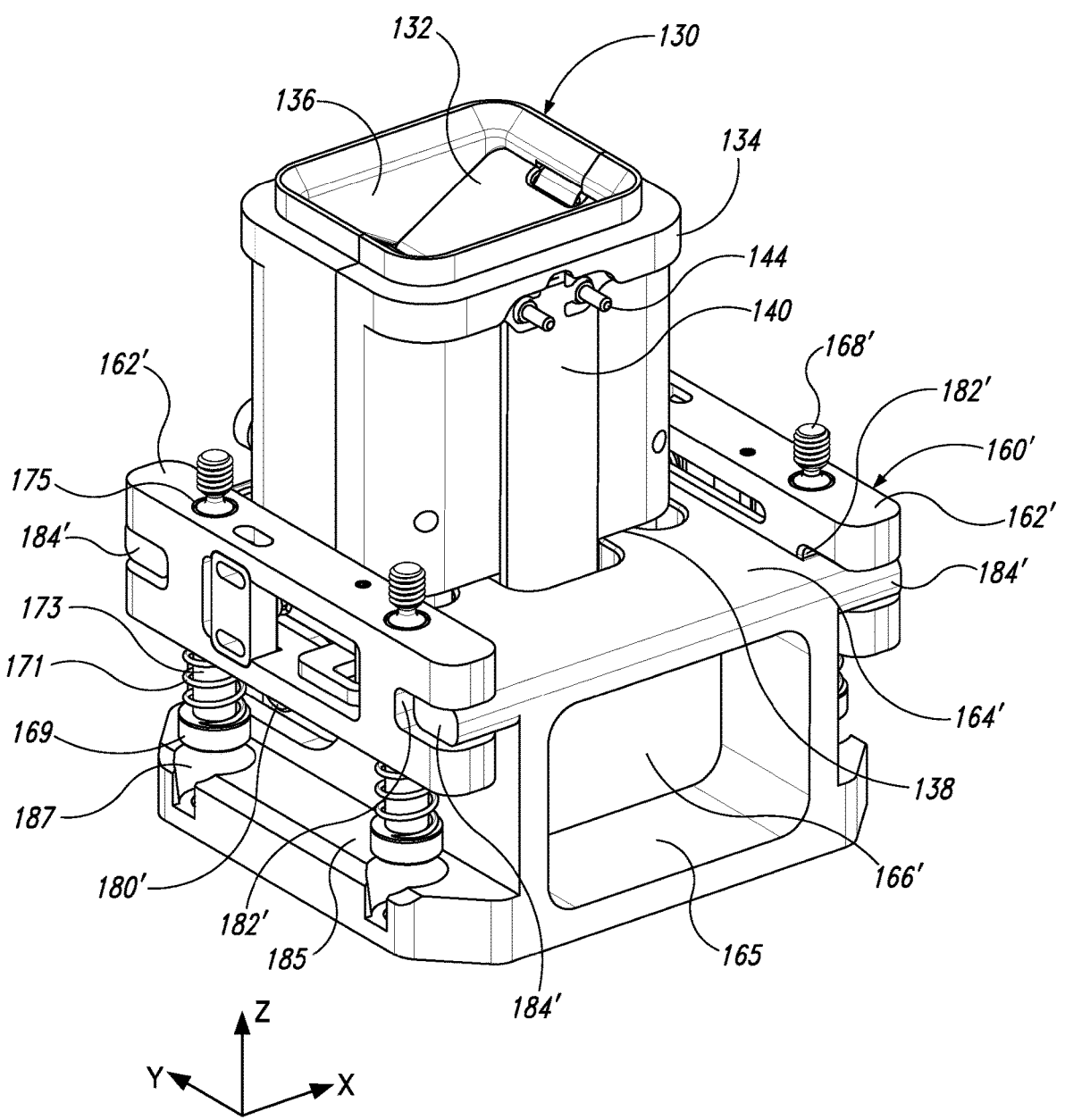
FIG. 5 is a perspective view of a carrier optical fiber connector and a floating fiber interface of the medical system of FIG. 1B configured in accordance with embodiments of the present technology.

FIGS. 4A-5 show aspects of the system 100 configured to reduce friction at the optical fiber connection between the medical instrument 104 and the instrument manipulator 120 (not shown here—see FIG. 2B). Referring first to FIG. 4A, for example, the carriage optical fiber connector 130 is shown removed from a housing or protective cover of the carriage 122 for purposes of illustration. The illustrated embodiment includes a floating fiber interface assembly ("floating fiber interface 160") retaining the carriage optical fiber connector 130, and together providing a friction-reducing assembly. The floating fiber interface 160 may provide various degrees of freedom to the carriage optical fiber connector 130 to move relative to the carriage 122 and reduce contact friction between the optical fiber connector 128 and the walls of the carriage optical fiber connector 130 during installation of the medical instrument 104. As noted above, the reduction of friction between the connectors may reduce particle generation and lower the risk of damage to the cleaved ends of the optical fibers.

The carriage optical fiber connector 130 may be positioned with respect to the carriage 122 such that only a connector well 136 of the carriage optical fiber connector 130 is visible (see FIG. 3). In this regard, as shown in FIGS. 4A and 4C, the housing or protective cover of the carriage 122 may interface with a connector lip 134 positioned on the carriage optical fiber connector 130 near the connector well 136. The connector lip 134 may be sized and configured to fill any gap forming around the connector well 136 to prevent debris and contaminants from entering internal areas of the carriage 122. In these embodiments, the degree of freedom of the floating fiber interface 160 can influence the size of the connector lip 134 such that the connector lip 134 prevents ingress of debris and contaminants as the floating fiber interface 160 reaches the limits of travel of the carriage optical fiber connector 130.

The floating fiber interface 160 may be configured to allow the carriage optical fiber connector 130 to translate in a floating plane (e.g., an X-Y plane, see FIG. 4B) with respect to the carriage 122. In the orientation shown in FIG. 4A, the floating fiber interface 160 generally only allows substantial movement of the carriage optical fiber connector 130 laterally, in the floating plane, with the normal of the floating plane being the direction of insertion of the instrument optical fiber connector 128 (e.g., the Z-direction), thereby providing sufficient support for the carriage optical fiber connector 130 during installation of the medical instrument 104. In some embodiments, the components of the floating fiber interface 160 have tolerances allowing a relatively small amount of movement in the directions other than the lateral translation (i.e., movement in the Z-direction, and rotation about the X, Y, and Z axes and combinations thereof).

The floating fiber interface 160 may include a pair of retention brackets 162 positioned in an opposing configuration lateral to the carriage optical fiber connector 130. The retention brackets 162 may be configured to support a translating socket 164 in the direction of insertion of the instrument optical fiber connector 128 (e.g., the Z-direction), and allow sliding translation in the floating plane (e.g., the X-Y plane). The retention brackets 162 may include slots 182 configured to constrain the translating socket 164 in the direction normal to the floating plane, and allow translation of the translating socket 164 confined within the floating plane. To enable such movement, the translating socket 164 may include tabs 184 extending into the slots 182 that are sized and configured to restrict movement in the direction normal to the floating plane, while allowing translation in the floating plane. In the illustrated embodiment, each of the retention brackets 162 includes two slots 182, and the translating socket 164 correspondingly has four tabs 184; however, in other embodiments, the floating fiber interface 160 includes any number of retention brackets 162, slots 182, and tabs 184 suitable for the desired degrees of freedom of the carriage optical fiber connector 130. The retention brackets 162 may further include various fasteners or other mounting features, such as screws 168, to couple the floating fiber interface 160 to the carriage 122. In this regard, the retention brackets 162 can be rigidly connected to the carriage 122, allowing translation of the carriage optical fiber connector 130 through movement of the translating socket 164 with respect to the retention brackets 162.

The translating socket 164 can further include a stabilizing extension 166 to resist substantial rotation of the carriage optical fiber connector 130 with respect to the floating plane (e.g., tipping of the carriage optical fiber connector 130). As shown in FIGS. 4C and 4D, for example, the carriage optical fiber connector 130 may have a ledge 138 that interfaces with the translating socket 164 to control the insertion depth of the carriage optical fiber connector 130 into the floating fiber interface 160. The configuration of the ledge 138 provides support for the carriage optical fiber connector 130 during installation of the medical instrument 104, while a locking feature, such as a set screw 180, may be included to prevent decoupling of the carriage optical fiber connector 130 and the floating fiber interface 160 during removal of the medical instrument 104. In the installed position, as shown in FIG. 4A, the ledge 138 interfaces with an upper surface of the translating socket 164 to set the insertion depth.

FIG. 4B is a cross-sectional view of the floating fiber interface 160, generally shown from a viewpoint normal to the plane of translation of the translating socket 164 (and with the carriage optical fiber connector 130 hidden for purposes of clarity). The translating socket 164 includes a connector opening 190 in which the carriage optical fiber connector 130 is inserted during assembly to the floating fiber interface 160. The retention brackets 162 generally capture the translating socket 164 in both directions normal to the plane of translation of the floating fiber interface 160; however, biased movement is allowed within the plane to lower the friction of the connectors during installation of the medical instrument 104. To provide the biased movement, the retention brackets 162 may each include biasing elements (e.g., coil springs 170 retained by spring retainers 172), which impart an opposing biasing force on the translating socket 164 through arms 174 protruding from the retention brackets 162. The distal end of the arms 174 include heads 176 configured to interface with the springs 170 on a first side, and cam sockets 178 of the translating socket 164 on a second side.

During translation of the translating socket 164 in the positive X-direction, the movement of the translating socket 164 toward one of the retention brackets 162 is transferred to the corresponding head 176 by the cam socket 178, deflecting one of the arms 174, and compressing the spring 170 against the spring retainer 172. The compression of the spring 170 in the direction of translation biases the translating socket 164 back to a neutral position where the spring forces equalize. In embodiments where both springs 170 are of equal spring force, the neutral position will be centered between the springs 170. The above movement in the positive X-direction also causes the translating socket 164 to move away from the other of the retention brackets 162, relieving pressure on the corresponding spring 170, which may cause the spring 170 to extend and deflect the arm 174 such that the head 176 stays in contact with the cam socket 178 during translation. In this regard, the arms 174 and the heads 176 both move mutually (e.g., in the same direction) with the movement of the translating socket 164, while one of the springs 170 is compressed and the other of the springs 170 is extended.

During translation of the translating socket 164 in the positive Y-direction, the nonlinear profile of the surface of the cam sockets 178 in the Y-direction causes each of the heads 176 to move away from the translating socket 164 in opposite directions from each other, deflecting the arms 174 away from each other. Thus arms 174 may act as cantilever springs. Deflection of the arms 174 away from each other may compress both of the springs 170 simultaneously, biasing the translating socket 164 back to the neutral position, generally in the valley of the illustrated profile of the cam sockets 178. In the illustrated configuration, translation of the translating socket 164 in the opposite, negative Y-direction has a similar effect on the heads 176, springs 170, and arms 174, again biasing the translating socket 164 back to the neutral position. In other embodiments, the profile the surface of the cam sockets 178 may have any suitable profile (e.g., linear, arcuate, etc.) configured to bias the translating socket 164 in the desired manner, and might not have equal biasing in the positive and negative Y-directions.

The floating fiber interface 160 may further include one or more features to limit the travel of the translating socket 164 in any of the degrees of freedom. As illustrated, for example, the floating fiber interface 160 may include stop pins 186 extending through one or both of the retention brackets 162. The stop pin 186 may extend through a travel limiting aperture 188 in the translating socket 164 sized and configured to set the limits of the translation of the translating socket 164. As shown, the stop pin 186 may be stationary as the translating socket 164 translates. At the desired limit of translation, the edge of the travel limiting aperture 188 contacts the stop pin 186 to stop translation of the translating socket 164. The aperture 188 is shown as a square to accordingly limit the travel in each of the X- and Y-directions, with a longer limit for combinations of translation in the X- and Y-directions; however, any travel limiting shape is within the scope of the present technology.

Turning to FIGS. 4C-4F, a friction-reducing embodiment of the carriage optical fiber connector 130 will now be explained in greater detail. The internal surfaces of the carriage optical fiber connector 130 and the cleaved end of an optical fiber 148 therein can be further protected from debris and contamination with a pair of opposing shutters 132 configured to substantially seal the internal well of the carriage optical fiber connector 130 when the instrument optical fiber connector 128 is not inserted. The optical fiber 148 can be constructed at least partially from silica or other similar materials. In some embodiments, the optical fiber 148 comprises a plurality of individual fibers. The shutters 132 may be biased toward the closed position. The shutters 132 can be pivotable to rotate toward the internal walls of the connector well 136 either by manual manipulation, e.g., upon insertion of the instrument optical fiber connector 128, or by an automated system, e.g., with actuators, motors, electromagnetic forces, etc. In embodiments having automated shutters 132, one or more sensors may be positioned and configured to send a signal to retract the shutters 132 when the instrument optical fiber connector 128 is in proximity, when the medical instrument 104 is being installed on the carriage 122, etc.

The shutters 132 can be constructed from a polymer, metal, composite, ceramic, and/or some other material or combination of materials. For example, the shutters 132 can be at least partially constructed from a metal (e.g., aluminum) plated with another metal (e.g., nickel). Contact between the instrument optical fiber connector 128 and the shutters 132, as well as subsequent rubbing/sliding between the instrument optical fiber connector 128 and the shutters 132, can create loose particles of the material of the instrument optical fiber connector 128 and/or of the shutters 132. Such particles can settle on the cleaved end of the optical fiber 148. The presence of particles on the cleaved end the optical fiber 148 can damage the optical fiber 148 when the instrument optical fiber connector 128 is fully connected to the carriage optical fiber connector 130. More specifically, the particles can be trapped between the optical fiber 148 of the carriage optical fiber connector 130 and an optical fiber of the instrument optical fiber connector 128. These particles can scratch, chip, and/or otherwise damage the exposed portions of the optical fiber 148. Damage to the optical fiber 148 can damage and/or destroy the quality and reliability of information passed through the optical fiber 148 from various components of the system 100.

Conventional remedies or solutions for avoiding the above-described particle damage include wiping the optical fiber 148 and/or a ferrule of the carriage optical fiber connector 130 with a cloth, swab, or other cleaning material. Other solutions include, for example, inserting a cleaning instrument into the carriage optical fiber connector 130 before connecting the instrument optical fiber connector 128 to the carriage optical fiber connector 130. While the solutions can be useful for removing pre-existing particles from the optical fibers, the solutions do not address or resolve generation of particles occurring during connection between the instrument optical fiber connector 128 and the carriage optical fiber connector 130.

As shown in FIGS. 4D-4F, the carriage optical fiber connector 130 configured in accordance with the present technology may further include a friction-reducing roller 146 positioned on at least one side of the connector well 136 of the carriage optical fiber connector 130. The roller 146 may be positioned to interface with and bias the instrument optical fiber connector 128 toward one side of the connector well 136 opposite the roller 146. In this regard, the roller may be biased by a cantilever spring 140 pinned at one end to the carriage optical fiber connector 130, e.g., with a fastener 142. The end of the cantilever spring 140 having the roller 146 may include a standoff feature 144 to provide clearance between the roller 146 and the cantilever spring 140 so the roller 146 can rotate freely during insertion of the instrument optical fiber connector 128. As shown in FIG. 4B, the connector opening 190 may include a relief cutout 192 to provide clearance for deflection of the cantilever spring 140 during insertion of the instrument optical fiber connector 128.

As the instrument optical fiber connector 128 is inserted into the carriage optical fiber connector 130, a portion of the instrument optical fiber connector 128 contacts the roller 146, progressively deflecting the cantilever spring 140 away from the connector well 136 (see FIG. 4F). The biasing force of the cantilever spring 140 urges the instrument optical fiber connector 128 toward the surface opposite the roller 146 during insertion, thereby reducing surface contact area between the instrument optical fiber connector 128 and the carriage optical fiber connector 130, which can reduce the opportunity for particle generation. In some embodiments, a plurality of rollers may be used to reduce friction between the instrument optical fiber connector 128 and the carriage optical fiber connector 130. Additional rollers 146 may be positioned on the same side, opposing sides, and/or adjacent sides of the connector well 136 from the roller 146. In these embodiments, the carriage optical fiber connector 130 may include two rollers on opposing sides of the connector well 136, two rollers on the same side of the connector well 136, one or more rollers on each of the four sides of the connector well 136, etc., or any combination thereof. The floating fiber interface 160 and the rollers 146 can be used independently or in conjunction with each other to reduce friction during installation of the medical instrument 104. In embodiments where the floating fiber interface 160 is used in conjunction with one or more rollers 146, aspects of each component may further reduce overall friction between the instrument optical fiber connector 128 and the carriage optical fiber connector 130.

FIG. 5 shows a perspective view of another embodiment of a floating fiber interface assembly ("floating fiber interface 160'") retaining the carriage optical fiber connector 130, and together providing a friction-reducing assembly. The floating fiber interface 160' has similarities to the floating fiber interface 160 of FIG. 4A, described above. As such, some features of the floating fiber interface 160' are denoted with a prime (') with like numbers corresponding to similar features of the floating fiber interface 160 of FIG. 4A, unless otherwise stated. The floating fiber interface 160' may provide various degrees of freedom to the carriage optical fiber connector 130 to move relative to the carriage 122 (FIG. 1B) and reduce contact friction between the optical fiber connector 128 and the walls of the carriage optical fiber connector 130 during installation of the medical instrument 104.

The floating fiber interface 160' may be configured to allow the carriage optical fiber connector 130 to translate in a floating plane (e.g., an X-Y plane, see FIG. 4B) and translate in the direction of insertion of the instrument optical fiber connector 128 (e.g., the Z-direction) with respect to the carriage 122.

The floating fiber interface 160' includes a pair of retention brackets 162' positioned in an opposing configuration lateral to the carriage optical fiber connector 130. The retention brackets 162' may be configured to support a translating socket 164' during sliding translation in the floating plane (e.g., the X-Y plane). The retention brackets 162' may include slots 182' configured to constrain the translating socket 164' in the direction normal to the floating plane, and allow translation of the translating socket 164' confined within the floating plane. To enable such movement, the translating socket 164' may include tabs 184' extending into the slots 182' that are sized and configured to restrict movement of the translating socket 164' with respect to the retention brackets 162' in the direction normal to the floating plane, while allowing translation in the floating plane (the translating socket 164' can also translate in the direction normal to the floating plane with respect to the carriage 122, as will be explained below).

In the illustrated embodiment, each of the retention brackets 162' includes two slots 182', and the translating socket 164' correspondingly has four tabs 184'; however, in other embodiments, the floating fiber interface 160' includes any number of retention brackets 162', slots 182', and tabs 184' suitable for the desired degrees of freedom of the carriage optical fiber connector 130. The retention brackets 162' may further include various fasteners or other mounting features, such as screws 168', to movably couple the floating fiber interface 160' to the carriage 122. The retention brackets 162' can be slidably connected to the carriage 122 by configuring the retention brackets 162' with apertures 175 sized and shaped to translate axially along a shaft portion 173 of the screws 168' (e.g., a threadless shoulder 173 of a shoulder screw 168' or other suitable fastener), which allows translation of the carriage optical fiber connector 130 in the insertion direction with respect to the carriage 122.

From the position of the floating fiber interface 160' shown in FIG. 5, biased movement of the carriage optical fiber connector 130 is allowed by movement of the floating fiber interface 160' in the direction of insertion of the instrument optical fiber connector 128 (e.g., the negative Z-direction). During such movement, the screws 168' are static with respect to the carriage 122 and the retention brackets 162' of the floating fiber interface 160' travel along the shaft portions 173 of the screws 168' until heads 169 of the screws 168' abut a lower surface of the retention brackets 162' to stop the translation. Insertion biasing elements (e.g., coil springs 171 retained by the heads 169) provide a connection force during insertion of the optical fiber connector 128 into the carriage optical fiber connector 130 (e.g., bias force in the positive Z-direction), thereby providing sufficient support for the carriage optical fiber connector 130 during installation of the medical instrument 104. In this regard, the coil springs 171 are configured to bias the heads 169 away from the retention brackets 162'. At the end of travel in the insertion direction, the heads 169 can optionally abut the retention brackets 162' to further ensure the fiber connection is made.

The translating socket 164' can include a lower flange portion 165 having extensions 185 in the direction of the screws 168'. The extensions 185 can include cavities 187 configured to receive at least a portion of the heads 169 of the screws 168' therein and retain the screws 168' with the floating fiber interface 160' until the screws 168' are threaded into the carriage 122. The retention of the screws 168' by the cavities 187 can also oppose the force of the coil springs 170 to retain the retention brackets 162' with the translating socket 164' until installation. The cavities 187 may have lower openings (not shown) that allow a tool (e.g., a hex wrench, not shown) to access the heads 169 for installation and removal of the screws 168'. The translating socket 164' can further include a stabilizing extension 166' to resist substantial rotation of the carriage optical fiber connector 130 with respect to the floating plane (e.g., tipping of the carriage optical fiber connector 130).

Figure 6:
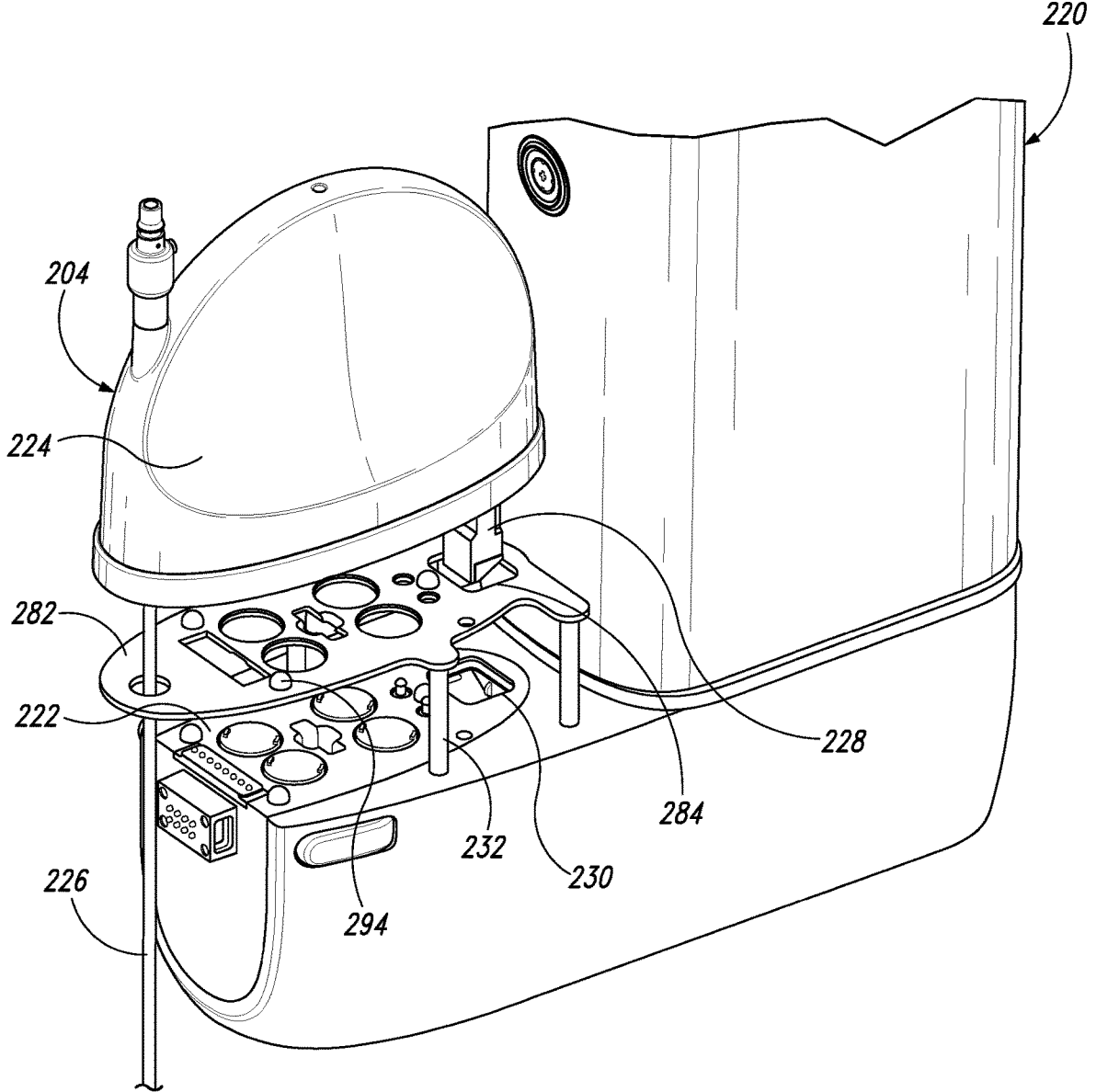
FIG. 6 is a perspective view of a translating alignment plate extending from the carriage of the manipulator assembly of FIG. 1B configured in accordance with an embodiment of the present technology.

FIG. 6 shows another embodiment of a friction-reducing interface between a medical instrument 204 and an instrument manipulator 220 configured for use with the system 100. The instrument manipulator 220 may include a translating alignment plate 282 coupled to an upper surface of the carriage 222. Certain features of the medical instrument 204 and the instrument manipulator 220 shown in FIG. 6 are similar to features of the medical instrument 104 and the instrument manipulator 120 of FIGS. 1A-3 described above. As such, the features of the medical instrument 204 and the instrument manipulator 220 are denoted in the 200-series with like numbers corresponding to similar features of the medical instrument 104 and the instrument manipulator 120 denoted in the 100-series, unless otherwise stated.

The translating alignment plate 282 may be configured to linearly translate from a first position above the upper surface of the carriage 222 where the instrument optical fiber connector 228 is not inserted into the carriage optical fiber connector 230, to a second position adjacent the carriage 222, where the instrument optical fiber connector 228 is inserted in the carriage optical fiber connector 230. The translating alignment plate 282 may include one or more telescoping standoffs 232 that constrain the translating alignment plate 282 to the linear translation. The standoffs 232 may be further configured to dampen translation of the translating alignment plate 282 for control of the rate of connection between the instrument optical fiber connector

228 and the carriage optical fiber connector 230, as high impulse connections can damage the cleaved ends of the fibers.

As illustrated in FIG. 6, the translating alignment plate 282 further includes an optical fiber connector pass-through 284 to receive the instrument optical fiber connector 228 as the medical instrument 204 is initially mated to the translating alignment plate 282 in the first position. The translating alignment plate 282 may also include one or more alignment indices 294 configured to position the medical instrument 204 with respect to the translating alignment plate 282 such that the instrument optical fiber connector 228 is generally aligned with the carriage optical fiber connector 230 as the translating alignment plate 282 moves from the first position to the second position. To form the connection between the instrument optical fiber connector 228 and the carriage optical fiber connector 230, the medical instrument 204 is first aligned and coupled to the translating alignment plate 282, and then the medical instrument 204 and the translating alignment plate 282 are simultaneously lowered from the first position to the second position, inserting the instrument optical fiber connector 228 into the carriage optical fiber connector 230. Lowering of the translating alignment plate 282 may be manual or automated, e.g., with one or more motors and sensors (not shown). In other embodiments, lowering of the translating alignment plate 282 may not be allowed until a cleaning of one or more system components is verified, either by a sensor (not shown) or manually. In some embodiments, shutters of the carriage optical fiber connector 230 may be configured to open (either automatically with a sensor/motor combination, or manually via a mechanical linkage) when the medical instrument 204 is coupled to the translating alignment plate 282.

The translating alignment plate 282 can be used independently or in conjunction with the floating fiber interface 160 and/or the rollers 146 of FIGS. 4A-4F to reduce friction during installation of the medical instrument 104. In embodiments where the translating alignment plate 282 is used in conjunction with the floating fiber interface 160 and/or one or more rollers 146, aspects of each component may further reduce overall friction between the instrument optical fiber connector 128 and the carriage optical fiber connector 130.

As the translating alignment plate 282 is lowered from the first position to the second position, various other mechanical and/or electrical connections are formed between the carriage 222 and the medical instrument 204. To facilitate the mechanical connections, the translating alignment plate 282 may include various openings for passing through movements of the controls of the instrument manipulator 220 such that the movements are relayed to the various receiving components of the medical instrument 204. Similarly, the translating alignment plate 282 may include electrical connectors to form connections between the instrument manipulator 220 and the medical instrument 204. In some embodiments, the translating alignment plate 282 has one or more intermediate components to transfer movement and/or signals of the instrument manipulator 220 to the medical instrument 204. In embodiments with intermediate components, the translating alignment plate 282 may serve as a clean connection for sterile environments, e.g., a drape coupled to a perimeter of the translating alignment plate 282.

Figure 7A:
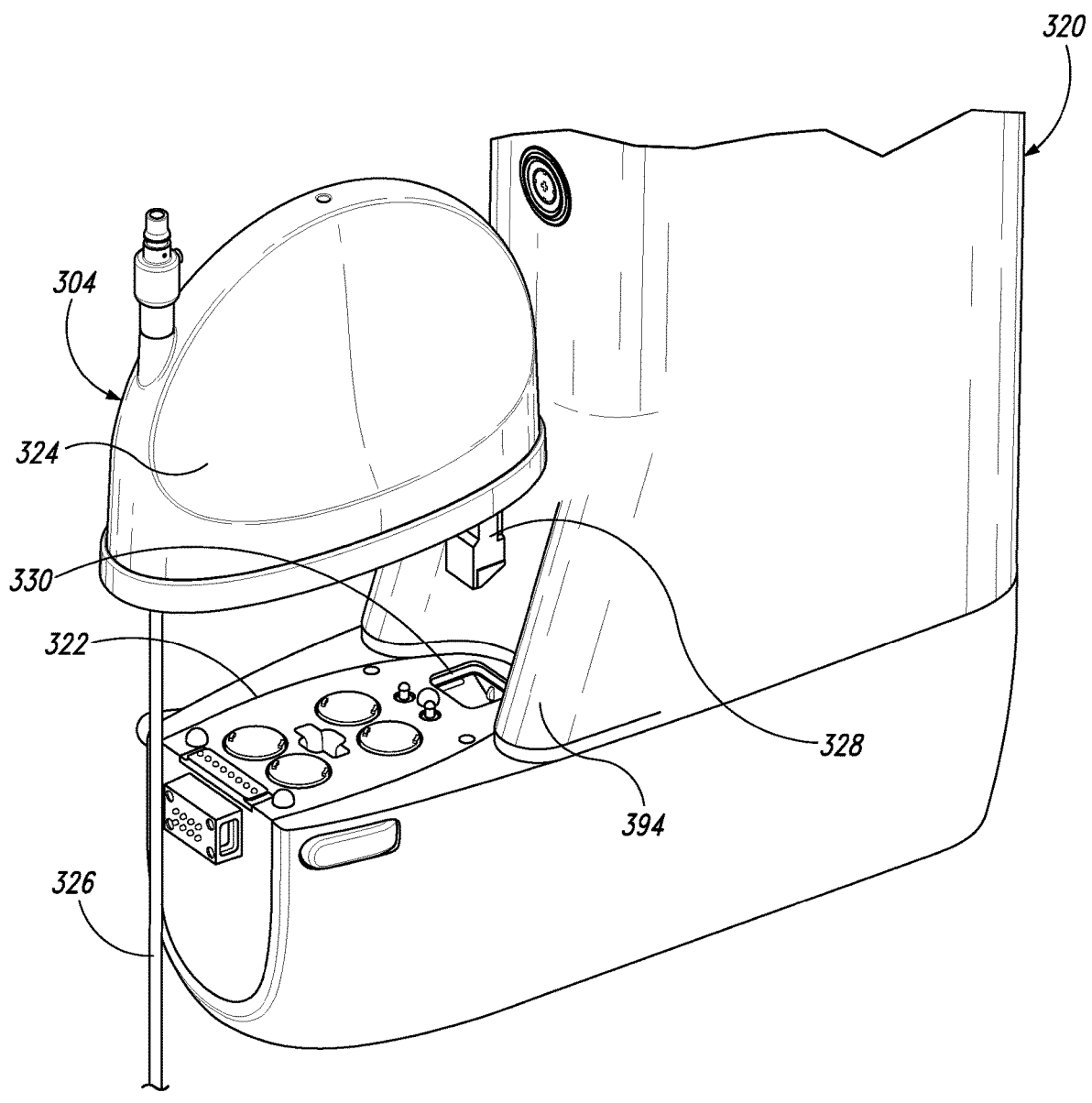
FIGS. 7A and 7B are perspective and plan views, respectively, of an alignment spar of the manipulator assembly of FIG. 1B configured in accordance with an embodiment of the present technology.
Figures 7B, 7C, 7D:
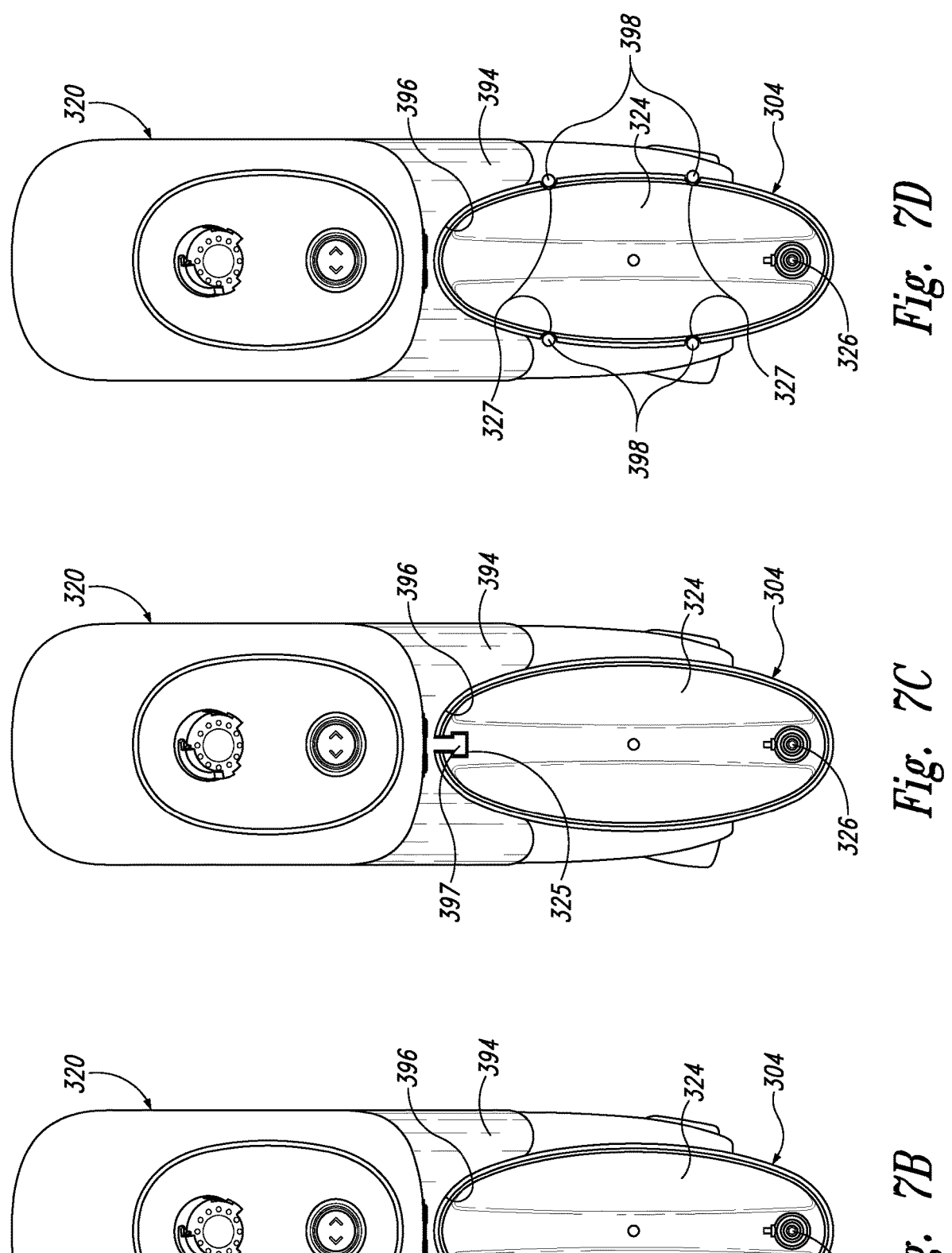
FIGS. 7C and 7D are plan views of the alignment spar of FIGS. 7A and 7B, showing embodiments of one or more clocking features.

FIGS. 7A and 7B show another embodiment of a friction-reducing interface between a medical instrument 304 and an instrument manipulator 320 configured for use with the system 100. The instrument manipulator 320 may include an alignment spar 394 positioned on the instrument manipulator 320 adjacent the carriage 322. Certain features of the medical instrument 304 and the instrument manipulator 320 shown in FIGS. 7A and 7B are similar to features of the medical instrument 104 and the instrument manipulator 120 of FIGS. 1A-3 described above, and as such, the features of the medical instrument 304 and the instrument manipulator 320 are denoted in the 300-series with like numbers corresponding to similar features of the medical instrument 104 and the instrument manipulator 120 denoted in the 100-series, unless otherwise stated.

The alignment spar 394 can protrude from a housing or protective cover of the instrument manipulator 320. As shown in FIG. 7B, the alignment spar 394 may have an engaging surface 396 that generally corresponds to the size, shape, and contour of an external surface of the instrument interface 324 of the medical instrument 304. Referring again to FIGS. 7A and 7B together, for example, the engaging surface 396 may be arcuate and configured to closely interface with the instrument interface 324 to guide the medical instrument 304 into alignment with the carriage 322 during insertion of the instrument optical fiber connector 328 into the carriage optical fiber connector 330. In this regard, as the operator O (not shown) installs the medical instrument 304 with the carriage 322, the operator O first engages the engaging surface 396 with the instrument interface 324 while the instrument optical fiber connector 328 is still disengaged from the carriage optical fiber connector 330. As the operator O lowers the medical instrument 304 (moving the medical instrument 304 toward the carriage 322), the instrument interface 324 maintains contact with the engaging surface 396 to provide course alignment of the instrument optical fiber connector 328 with the carriage optical fiber connector 330. As the medical instrument 304 is further moved toward the carriage 322 (and the instrument interface 324 maintains contact with the engaging surface 396), friction between the instrument optical fiber connector 328 and the carriage optical fiber connector 330 may be reduced when they contact each other during insertion, because they may be coarsely aligned before contact.

FIG. 7C shows another embodiment of a friction-reducing interface between the medical instrument 304 and the instrument manipulator 320 configured for use with the system 100. In some embodiments, the engaging surface 396 may include a clocking feature, e.g., a keyed slot 325 extending through in the instrument interface 324 and configured to interface with a keyed protrusion 397 extending from the engaging surface 396 of the instrument manipulator 320. The interface of the keyed slot 325 and the keyed protrusion 397 is configured to orient the medical instrument 304 with respect to the carriage 322. Although the keyed protrusion 397 is shown extending from the engaging surface 396 in FIG. 7C, in other embodiments, the keyed protrusion 397 may be used to orient the medical instrument 304 without the alignment spar 394, in which the keyed protrusion 397 may extend from the instrument manipulator 320.

FIG. 7D shows another embodiment of a friction-reducing interface between the medical instrument 304 and the instrument manipulator 320 configured for use with the system 100. In some embodiments, the carriage 322 may include a clocking feature, e.g., a pin 398 extending from the carriage 322 and configured to interface with an indentation 327 in the instrument interface 324. The interface of the indentation 327 and the pin 398 is configured to orient the medical instrument 304 with respect to the carriage 322. As shown, a plurality of pins 398 and corresponding indentations 327 may be used to orient the medical instrument 304 with respect to the carriage 322. In other embodiments, the pins 398 are tapered to gradually orient the medical instrument 304 as the medical instrument 304 is lowered toward the carriage 322. Although the pin 398 is shown extending from the instrument manipulator 320 having the alignment spar 394, in other embodiments, the pin 398 may be used to orient the medical instrument 304 without the alignment spar 394.

The alignment spar 394 can be used independently or in conjunction with the floating fiber interface 160, the rollers 146, and/or the translating alignment plate 282 of FIGS. 4A-5, and/or with the clocking features of FIGS. 7C and 7D, to reduce friction during installation of the medical instrument 104. In embodiments where the alignment spar 394 is used in conjunction with the floating fiber interface 160, one or more rollers 146, and/or the translating alignment plate 282, aspects of each component may further reduce overall friction between the instrument optical fiber connector 128 and the carriage optical fiber connector 130.

Figure 8:
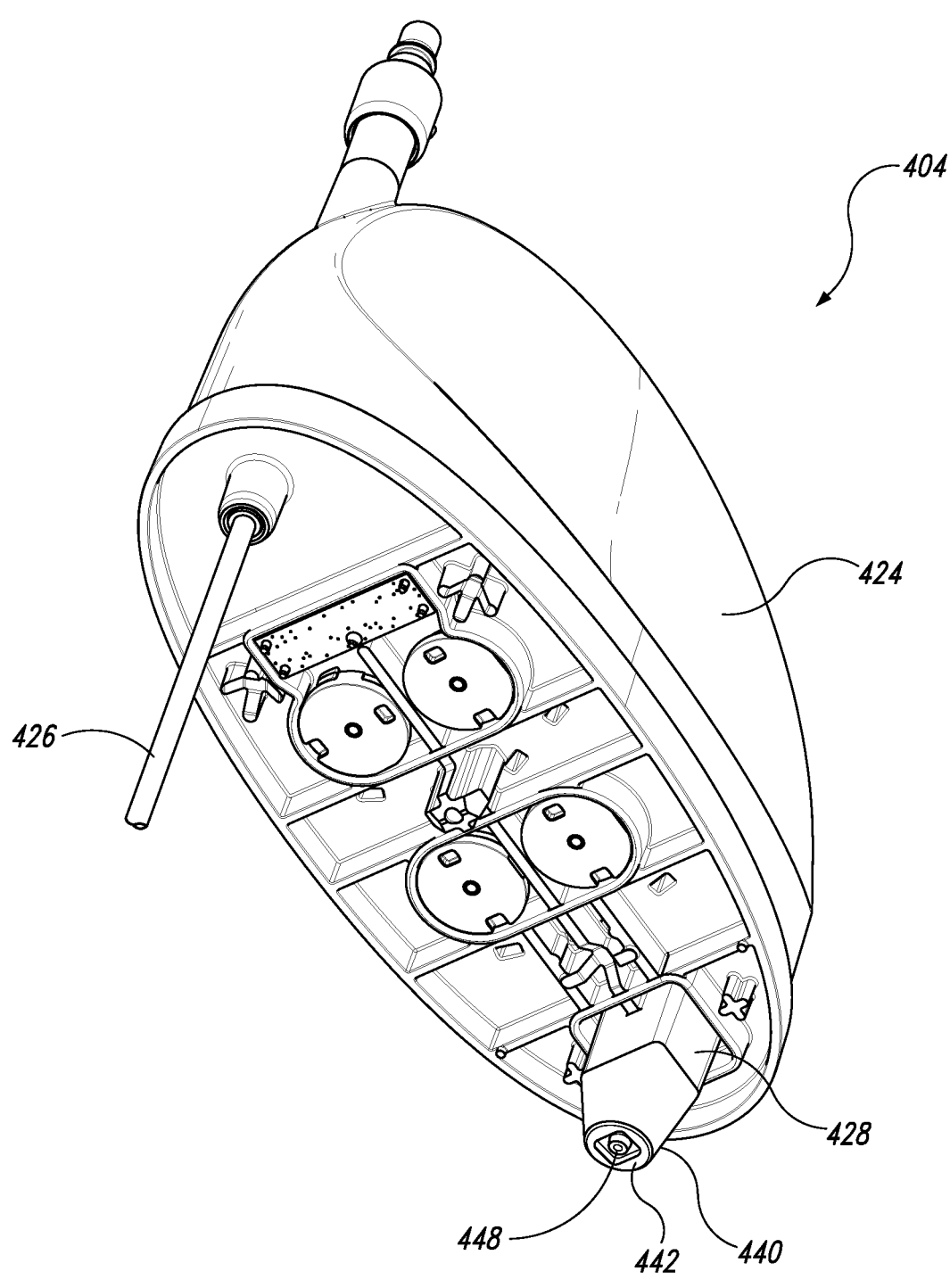
FIG. 8 is a perspective view of an instrument optical fiber connector of a medical instrument of the medical system of FIG. 1B the instrument optical fiber connector having a conical kinematic surface configured in accordance with an embodiment of the present technology.

FIG. 8 shows another embodiment of a friction-reducing interface between a medical instrument 404 configured for use with the system 100. The instrument optical fiber connector 428 may include a conical kinematic surface 440 positioned on a distal end portion of the instrument optical fiber connector 428. Certain features of the medical instrument 404 shown in FIG. 8 are similar to features of the medical instrument 104 of FIGS. 1A-3 described above. As such, the features of the medical instrument 404 are denoted in the 400-series with like numbers corresponding to similar features of the medical instrument 104 denoted in the 100-series, unless otherwise stated.

As shown, the conical kinematic surface 440 can be frustoconical, tapering from an outer surface of the instrument optical fiber connector 428 to a tip 442 at the distal end of the instrument optical fiber connector 428 near the optical fiber 448. During installation of the medical instrument 404 to the carriage of the instrument manipulator (not shown), the smaller size of the tip 442 compared to body of the instrument optical fiber connector 428, allows a greater initial range of alignment with the carriage optical fiber connector. As the instrument optical fiber connector 428 is further inserted into the carriage optical fiber connector, the conical kinematic surface 440 brings the instrument optical fiber connector 428 into alignment, thereby allowing insertion into the carriage optical fiber connector. The conical kinematic surface 440 can provide an alignment constraint of the medical instrument 404 to the carriage 422. As such, an alignment constraint feature of the instrument interface 424 may be excluded such that the connection of the medical instrument 404 to the carriage 422 is not over-constrained. In other embodiments, the kinematic surface 440 may be any suitable shape to guide the instrument optical fiber connector 428 into the carriage optical fiber connector, including a tapering square, oval, triangle, etc.

The conical kinematic surface 440 can be used independently or in conjunction with the floating fiber interface 160, the rollers 146, the translating alignment plate 282, and/or alignment spar 394 of FIGS. 4A-7B to reduce friction during installation of the medical instrument 104. In embodiments where the conical kinematic surface 440 is used in conjunction with the floating fiber interface 160, one or more rollers 146, the translating alignment plate 282, and/or the alignment spar 394, aspects of each component may further reduce overall friction between the instrument optical fiber connector 128 and the carriage optical fiber connector 130.

EXAMPLES

Several aspects of the present technology are set forth in the following examples:

1. A floating connector interface, comprising:
    a retention bracket having a slot;
    a translating socket slidingly associated with the retention bracket, the translating socket comprising:
        a tab portion extending into the slot to permit translation of the translating socket with respect to the retention bracket, wherein the translation is confined within a floating plane; and
        an aperture configured to receive a carriage connector; and
    a biasing element positioned between the retention bracket and the translating socket, wherein the biasing element is configured to resist translation of the translating socket.

2. The floating connector interface of example 1, wherein the retention bracket comprises a first retention bracket, the slot comprises a first slot, and the tab portion of the translating socket comprises a first tab portion, and wherein the floating connector interface further comprises:
    a second retention bracket positioned on an opposite edge of the translating socket from the first retention bracket, the second retention bracket having a second slot configured to receive a second tab portion of the translating socket and permit translation of the translating socket with respect to the first and second retention brackets.

3. The floating connector interface of example 2, wherein the biasing element comprises a first biasing element, and wherein the floating connector interface further comprises a second biasing element positioned between the second retention bracket and the translating socket, wherein the second biasing element is positioned to oppose the first biasing element.

4. The floating connector interface of example 3, wherein the first and second biasing elements have opposing biasing forces to urge the translating socket to a neutral position in a direction aligned with the biasing forces.

5. The floating connector interface of example 3 or example 4, wherein the first and second biasing elements comprise coil springs.

6. The floating connector interface of any of examples 2-5, wherein the first retention bracket further comprises a first arm and the second retention bracket further comprises a second arm, and wherein the first and second arms are configured to mutually deflect with movement of the translating socket in a direction aligned with the biasing forces.

7. The floating connector interface of example 6, wherein:
    the first arm further comprises a first head on a distal end of the first arm,
    the second arm further comprises a second head on a distal end of the second arm,
    the translating socket further comprises a first cam socket configured to interface with the first head and a second cam socket configured to interface with the second head, and
    the first and second cam sockets have cam profiles configured to deflect the first and second arms away from one another during movement of the translating socket in a direction perpendicular to the biasing forces.

8. The floating connector interface of example 7, wherein the cam profiles are shaped such that the biasing forces urge the translating socket to a neutral position in the direction perpendicular to the biasing forces.

9. The floating connector interface of any of examples 1-8, wherein:
    the retention bracket has an aperture configured to slidingly receive a fastener therein such that the retention bracket can translate axially along the fastener;
    the floating connector interface further comprises an insertion biasing element positioned between the retention bracket and a head of the fastener, and
    the insertion biasing element is configured to bias the head of the fastener away from the retention bracket.

10. The floating connector interface of any of examples 1-9, wherein the floating connector interface comprises a floating optical fiber connector interface, and wherein the carriage connector comprises a carriage optical fiber connector.

11. A carriage, comprising:
    a retention bracket having a slot;
    a translating socket slidingly associated with the retention bracket, the translating socket comprising a tab portion extending into the slot to permit translation of the translating socket with respect to the carriage, wherein the translation is confined within a floating plane;
    a carriage connector having a housing removably couplable to an aperture in the translating socket; and
    a biasing element positioned between the retention bracket and the translating socket, wherein the biasing element is configured to resist translation of the translating socket, and wherein a direction of insertion of an instrument connector into the carriage connector is normal to the floating plane.

12. The carriage of example 11, wherein the retention bracket comprises a first retention bracket, the slot comprises a first slot, and the tab portion of the translating socket comprises a first tab portion, and wherein the carriage further comprises:
    a second retention bracket positioned on an opposite edge of the translating socket from the first retention bracket, the second retention bracket having a second slot configured to receive a second tab portion of the translating socket and permit translation of the translating socket with respect to the first and second retention brackets.

13. The carriage of example 12, wherein the biasing element comprises a first biasing element, and wherein the carriage further comprises a second biasing element positioned between the second retention bracket and the translating socket, the second biasing element positioned to oppose the first biasing element.

14. The carriage of example 13, wherein the first and second biasing elements have opposing biasing forces to urge the translating socket to a neutral position in a direction aligned with the biasing forces.

15. The carriage of example 13 or example 14, wherein the first and second biasing elements comprise coil springs.

16. The carriage of any of examples 12-15, wherein the first retention bracket further comprises a first arm and the second retention bracket further comprises a second arm, and wherein the first and second arms are configured to mutually deflect with movement of the translating socket in a direction aligned with the biasing forces.

17. The carriage of example 16, wherein:

the first arm has a first head on a distal end of the first arm and the second arm has a second head on a distal end of the second arm, the translating socket further comprises a first cam socket configured to interface with the first head and a second cam socket configured to interface with the second head, and the first and second cam sockets have cam profiles configured to deflect the first and second arms away from one another during movement of the translating socket in a direction perpendicular to the biasing forces.

18. The carriage of example 17, wherein the cam profiles are shaped such that the biasing forces urge the translating socket to a neutral position in the direction perpendicular to the biasing forces.

19. The carriage of any of examples 11-18, wherein:

the retention bracket further comprises an aperture configured to slidingly receive a fastener therein such that the retention bracket can translate axially along the fastener;

the carriage further comprises an insertion biasing element positioned between the retention bracket and a head of the fastener; and the insertion biasing element is configured to bias the head of the fastener away from the retention bracket.

20. The carriage of any of examples 11-19, further comprising a roller positioned on a first side of a well of the housing, wherein the roller is biased toward the well with a cantilever spring.

21. The carriage of example 20, wherein the aperture comprises a cutout for clearance of the cantilever spring.

22. The carriage of example 20 or example 21, further comprising a second roller positioned on a second side of the well opposite the first side of the well, wherein the second roller is biased toward the first roller with a second cantilever spring.

23. The carriage of example 22, further comprising a third roller positioned on a third side of the well adjacent to either of the first or second sides of the well, wherein the third roller is biased toward the well with a third cantilever spring.

24. The carriage of example 23, further comprising a fourth roller positioned on a fourth side of the well opposite the third side of the well, wherein the fourth roller is biased toward the third roller with a fourth cantilever spring.

25. The carriage of any of examples 22-24, wherein the carriage connector further comprises shutters positioned in the well.

26. The carriage of any of examples 11-25, wherein the housing has a ledge configured to interface with the translating socket to control an insertion depth of the carriage connector within the aperture.

27. The carriage of any of examples 11-26, wherein the translating socket has a locking feature to retain the housing within the aperture.

28. The carriage of any of examples 11-27, wherein the floating connector interface comprises a floating optical fiber connector interface, and wherein the carriage connector comprises a carriage optical fiber connector.

29. A connector alignment apparatus, comprising:

a carriage having a carriage optical fiber connector, a plate configured to removably retain an instrument interface in alignment for connection to the carriage, the plate having an aperture configured to receive an instrument optical fiber connector; and a telescoping standoff coupled between the plate and the carriage, wherein the telescoping standoff is operable to position the plate at a first position in which the plate is spaced apart from the carriage and to position the plate at a second position in which the plate is adjacent to the carriage.

30. The connector alignment apparatus of example 29, wherein the aperture is configured to position the instrument optical fiber connector in alignment with the carriage optical fiber connector when the plate is in the first position.

31. The connector alignment apparatus of example 29 or example 30, wherein the telescoping standoff is operable to linearly translate the plate between the first position and the second position.

32. The connector alignment apparatus of any of examples 29-31, wherein the instrument optical fiber connector is connected to the carriage optical fiber connector when the plate is in the second position.

33. The connector alignment apparatus of any of examples 29-32, wherein movement of the telescoping standoff is damped.

34. The connector alignment apparatus of any of examples 29-32, wherein the telescoping standoff further includes one or more springs to apply a biasing force to the plate toward the first position.

35. The connector alignment apparatus of example 29, wherein movement of the plate is automated.

36. The connector alignment apparatus of any of examples 29-35, wherein the plate further comprises connectors configured to pass one or more of mechanical movement or electrical signals between the instrument interface and the carriage.

37. The connector alignment apparatus of any of examples 29-36, wherein the plate is adjustable to align the instrument interface to the carriage.

38. The connector alignment apparatus of any of examples 29-37, wherein the plate further comprises one or more intermediate components configured to transfer mechanical movement from the carriage to the instrument interface.

39. The connector alignment apparatus of any of examples 29-38, wherein the plate has clean connection features.

40. The connector alignment apparatus of any of examples 29-39, further comprising a drape connected to a perimeter of the plate.

41. An alignment system, comprising:

a carriage having a housing and a carriage optical fiber connector;

an instrument interface having an outer surface and an instrument optical fiber connector configured to connect to the carriage optical fiber connector when the instrument interface is mated to the carriage; and an alignment spar protruding from the housing of the carriage, the alignment spar having a shape corresponding to the outer surface of the instrument interface and configured to align the instrument interface and the carriage such that the instrument optical fiber connector is aligned with the carriage optical fiber connector.

42. The alignment system of example 41, wherein the alignment spar is integrated into the housing.

43. The alignment system of example 41 or example 42, wherein the alignment spar is arcuate.

44. The alignment system of example 41, wherein the housing further comprises a keyed protrusion extending from the housing and the instrument interface further comprises a keyed slot configured to interface with the keyed protrusion, wherein the interface of the keyed slot and keyed protrusion is configured to orient the instrument interface to the carriage during connection of the instrument optical fiber connector and the carriage optical fiber connector.

45. The alignment system of example 43, wherein the keyed protrusion extends from the alignment spar.

46. The alignment system of example 41, wherein the carriage further comprises a pin and the instrument interface further comprises an indentation configured to interface with the pin, wherein the interface of the indentation and the pin is configured to orient the instrument interface to the carriage during connection of the instrument optical fiber connector and the carriage optical fiber connector.

47. The alignment system of example 45, wherein the carriage comprises a plurality of the pins and the housing comprises a plurality of the indentations corresponding to the plurality of pins.

48. The alignment system of example 46 or example 47, wherein the pin is tapered.

49. The alignment system of example 41, wherein the carriage optical fiber connector is coupled to a floating optical fiber connector interface of example 1.

50. An instrument, comprising:
   an instrument interface; and
   an instrument optical fiber connector protruding from the instrument interface, the instrument optical fiber connector comprising:
      a connector body having an outer surface configured to interface with a carriage optical fiber connector; and
      a conical kinematic surface positioned on a distal end portion of the connector body, the conical kinematic surface tapering down from the outer surface of the connector body to a tip of the connector body, wherein the conical kinematic surface is configured to align the instrument optical fiber connector and the carriage optical fiber connector during installation of the instrument interface.

51. The instrument of example 50, wherein the conical kinematic surface comprises a frustoconical kinematic surface.

52. The instrument of example 50 or example 51, wherein a shape of the conical kinematic surface comprises one or more of a tapering square, a tapering oval, or a tapering triangle.

53. The instrument of any of examples 50-52, wherein the carriage optical fiber connector is coupled to a floating optical fiber connector interface of example 1.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

For ease of reference, identical reference numbers are used to identify similar or analogous components or features throughout this disclosure, but the use of the same reference number does not imply that the features should be construed to be identical. Indeed, in many examples described herein, identically numbered features have a plurality of embodiments that are distinct in structure and/or function from each other. Furthermore, the same shading may be used to indicate materials in cross section that can be compositionally similar, but the use of the same shading does not imply that the materials should be construed to be identical unless specifically noted herein.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A floating connector interface, comprising:
   a first retention bracket including a first slot;
   a second retention bracket including a second slot;
   a translating socket slidingly supported between the first retention bracket and the second retention bracket, the translating socket comprising:
      a first tab portion extending into the first slot and a second tab portion extending into the second slot to permit translation of the translating socket with respect to the first and second retention brackets, wherein the translation is confined within a floating plane; and
      an aperture configured to receive a carriage connector; and
   a biasing element positioned between the first retention bracket and the translating socket, wherein the biasing element is configured to resist translation of the translating socket.

2. The floating connector interface of claim 1, wherein the biasing element is a first biasing element, and wherein the floating connector interface further comprises a second biasing element positioned between the second retention bracket and the translating socket, wherein the second biasing element is positioned to oppose the first biasing element.

3. The floating connector interface of claim 2, wherein the first and second biasing elements have opposing biasing forces to urge the translating socket to a neutral position in a direction aligned with the biasing forces.

4. The floating connector interface of claim 2, wherein the first and second biasing elements comprise coil springs.

5. The floating connector interface of claim 1, wherein the first retention bracket further comprises a first arm and the second retention bracket further comprises a second arm, and wherein the first and second arms are configured to mutually deflect with movement of the translating socket in a direction aligned with the biasing forces.

6. The floating connector interface of claim 5, wherein:
the first arm further comprises a first head on a distal end of the first arm,
the second arm further comprises a second head on a distal end of the second arm,
the translating socket further comprises a first cam socket configured to interface with the first head and a second cam socket configured to interface with the second head, and
the first and second cam sockets have cam profiles configured to deflect the first and second arms away from one another during movement of the translating socket in a direction perpendicular to the biasing forces.

7. The floating connector interface of claim 6, wherein the cam profiles are shaped such that the biasing forces urge the translating socket to a neutral position in the direction perpendicular to the biasing forces.

8. The floating connector interface of claim 1, wherein:
the first retention bracket has a bracket aperture configured to slidingly receive a fastener therein such that the first retention bracket can translate axially along the fastener;
the floating connector interface further comprises an insertion biasing element positioned between the first retention bracket and a head of the fastener; and
the insertion biasing element is configured to bias the head of the fastener away from the first retention bracket.

9. The floating connector interface of claim 1, wherein the floating connector interface comprises a floating optical fiber connector interface, and wherein the carriage connector comprises a carriage optical fiber connector.

10. A carriage, comprising:
a first retention bracket including a first slot;
a second retention bracket including a second slot;
a translating socket slidingly supported between the first retention bracket and the second retention bracket, the translating socket comprising a first tab portion extending into the first slot and a second tab portion extending into the second slot to permit translation of the translating socket with respect to the first and second retention brackets, wherein the translation is confined within a floating plane;
a carriage connector having a housing removably couplable to an aperture in the translating socket; and
a biasing element positioned between the first retention bracket and the translating socket, wherein the biasing element is configured to resist translation of the translating socket, and wherein a direction of insertion of an instrument connector into the carriage connector is normal to the floating plane.

11. The carriage of claim 10, wherein the biasing element is a first biasing element, and wherein the carriage further comprises a second biasing element positioned between the second retention bracket and the translating socket, the second biasing element positioned to oppose the first biasing element.

12. The carriage of claim 11, wherein the first and second biasing elements have opposing biasing forces to urge the translating socket to a neutral position in a direction aligned with the biasing forces.

13. The carriage of claim 11, wherein the first and second biasing elements comprise coil springs.

14. The carriage of claim 10, wherein the first retention bracket further comprises a first arm and the second retention bracket further comprises a second arm, and wherein the first and second arms are configured to mutually deflect with movement of the translating socket in a direction aligned with the biasing forces.

15. The carriage of claim 14, wherein:
the first arm has a first head on a distal end of the first arm and the second arm has a second head on a distal end of the second arm,
the translating socket further comprises a first cam socket configured to interface with the first head and a second cam socket configured to interface with the second head, and
the first and second cam sockets have cam profiles configured to deflect the first and second arms away from one another during movement of the translating socket in a direction perpendicular to the biasing forces.

16. The carriage of claim 15, wherein the cam profiles are shaped such that the biasing forces urge the translating socket to a neutral position in the direction perpendicular to the biasing forces.

17. The carriage of claim 10, wherein:
the first retention bracket further comprises bracket aperture configured to slidingly receive a fastener therein such that the first retention bracket can translate axially along the fastener;
the carriage further comprises an insertion biasing element positioned between the first retention bracket and a head of the fastener; and
the insertion biasing element is configured to bias the head of the fastener away from the first retention bracket.

18. The carriage of claim 10, wherein the carriage connector comprises a carriage optical fiber connector.

19. A floating optical fiber connector interface, comprising:
a retention bracket including a slot;
a translating socket slidingly associated with the retention bracket, the translating socket comprising:
a tab portion extending into the slot to permit translation of the translating socket with respect to the retention bracket, wherein the translation is confined within a floating plane; and
an aperture configured to receive a carriage optical fiber connector; and
a biasing element positioned between the retention bracket and the translating socket, wherein the biasing element is configured to resist translation of the translating socket.

20. The floating optical fiber connector interface of claim 19, wherein:

the retention bracket has a bracket aperture configured to slidingly receive a fastener therein such that the retention bracket can translate axially along the fastener;

the floating optical fiber connector interface further comprises an insertion biasing element positioned between the retention bracket and a head of the fastener; and the insertion biasing element is configured to bias the head of the fastener away from the retention bracket.

\* \* \* \* \*